(12) United States Patent
Monzyk et al.

(10) Patent No.: US 6,866,755 B2
(45) Date of Patent: Mar. 15, 2005

(54) PHOTOLYTIC ARTIFICIAL LUNG

(75) Inventors: Bruce F. Monzyk, Delaware, OH (US); Kurt Dasse, Wellesley, MA (US)

(73) Assignees: Battelle Memorial Institute, Columbus, OH (US); Pharos, LLC, Waltham, MA (US)

( * ) Notice: Subject to any disclaimer, the term of this patent is extended or adjusted under 35 U.S.C. 154(b) by 0 days.

(21) Appl. No.: 09/920,385

(22) Filed: Aug. 1, 2001

(65) Prior Publication Data
US 2003/0074062 A1 Apr. 17, 2003

(51) Int. Cl.$^7$ ................................................ C25B 9/00
(52) U.S. Cl. ........................................................ 204/252
(58) Field of Search .............................. 204/242, 252; 205/340

(56) References Cited

U.S. PATENT DOCUMENTS

| | | | |
|---|---|---|---|
| 3,533,408 A | 10/1970 | Paoli | |
| 4,011,149 A | * 3/1977 | Nozik | ............ 205/340 |
| 4,244,824 A | 1/1981 | Lange et al. | |
| 4,306,018 A | 12/1981 | Kirkpatrick | |
| 4,309,463 A | 1/1982 | Lange et al. | |
| 4,466,869 A | * 8/1984 | Ayers | ............ 205/340 |
| 4,643,817 A | * 2/1987 | Appleby | ............ 204/242 |
| 4,790,916 A | * 12/1988 | Murphy et al. | ............ 205/340 |
| 4,793,910 A | 12/1988 | Smotkin et al. | |
| 4,889,604 A | 12/1989 | Khan et al. | |
| 4,968,483 A | 11/1990 | Muller et al. | |
| 5,174,877 A | 12/1992 | Cooper et al. | |
| 5,262,023 A | 11/1993 | Sayama et al. | |
| 5,294,315 A | 3/1994 | Cooper et al. | |
| 5,294,401 A | 3/1994 | Hagiwara | |
| 5,366,696 A | 11/1994 | Williams | |
| 5,614,378 A | 3/1997 | Yang et al. | |
| 5,779,912 A | 7/1998 | Gonzalez-Martin et al. | |
| 5,865,960 A | 2/1999 | Park et al. | |
| 5,964,725 A | 10/1999 | Sato et al. | |
| 6,042,875 A | 3/2000 | Ding et al. | |
| 6,051,194 A | 4/2000 | Peill et al. | |
| 6,136,186 A | 10/2000 | Gonzalez-Martin et al. | |
| 6,183,695 B1 | 2/2001 | Godec et al. | |

FOREIGN PATENT DOCUMENTS

| | | | |
|---|---|---|---|
| WO | WO 01/70396 A3 | 9/2001 | |
| WO | WO 01/70396 A2 | 9/2001 | |

\* cited by examiner

*Primary Examiner*—Donald R. Valentine
(74) *Attorney, Agent, or Firm*—Fay, Sharpe, Fagan, Minnich & McKee, LLP

(57) ABSTRACT

The present invention is directed to a photolytic artificial lung. The photolytic artificial lung converts water to oxygen for blood absorption, regulates pH, the removes carbon dioxide, and co-produces electrical power is disclosed. The photolytic artificial lung includes a photolytic cell where all of the chemical reactions occur. The photolytic cell disclosed herein can also be used to direct chemical reactions in organs other than the lung. Also disclosed herein is a gas sorption device for removing carbon dioxide from the system by chemical sorption.

13 Claims, 10 Drawing Sheets

PHOTOLYTIC ARTIFICIAL LUNG

FIELD OF THE INVENTION

The present invention is directed to a photolytic artificial lung that utilizes light energy to achieve physiological gas exchange in fluids, such as in the blood stream of a patient experiencing respiratory difficulties, and to a photolytic cell used for the same. It finds particular applications in conjunction in the field of artificial organs and the medical arts. However, it is to be appreciated, that the invention will also find applications in related fields due to the photo-electro chemical transformations involved therein.

BACKGROUND OF THE INVENTION

The lung is the main organ in the respiratory system, in which venous blood is relieved of carbon dioxide and oxygenated by air drawn through the trachea and bronchi into the alveoli. There are two lungs, a right and a left, the former consisting of three, the latter of two, lobes. The lungs are situated in the thoracic cavity and are enveloped by the pleura.

In humans, each lung is connected with the pharynx through the trachea and larynx. The base rests on the diaphragm and the apex rises slightly above the sternal end of the first rib. The lungs include the lobes, lobules, bronchi, bronchioles, infundibula, and alveoli or air sacs.

The lungs contain about 300 million alveoli and their respiratory surface is about 70 square meters. Adults average about 15–20 respirations per minute. The total capacity of the lung varies from about 3.6 to 9.4 liters in adult men and about 2.5 to 6.9 in adult women.

The left lung has an indentation, called the cardiac depression, for the normal placement of the heart. Behind this is the hilum, through which the blood vessels, lymphatics, and bronchi enter and leave the lung.

Air travels from the mouth and nasal passage to the pharynx and the trachea. Two main bronchi, one on each side, extend from the trachea. The main bronchi divide into smaller bronchi, one for each of five lobes. These further divide into a great number of smaller bronchioles. Additionally, there are about 50 to 80 terminal bronchioles in each lobe. Each of these divides into two respiratory bronchioles, which in turn divide to form 2 to 11 alveolar ducts. The alveolar sacs and alveoli arise from these ducts. The spaces between the alveolar sacs and alveoli are called atria.

The alveolus is the point at which the blood and inspired air are separated only by a very thin wall or membrane that allows oxygen and nitrogen to diffuse into the blood and carbon dioxide and other gases to pass from the blood into the alveoli. The alveoli contain small pores that serve to connect adjacent alveoli to each other.

The primary purpose of the lung is to bring air and blood into intimate contact so that oxygen can be added to the blood and carbon dioxide can be removed. This is achieved by two pumping systems, one moving a gas and the other a liquid. The blood and air are brought together so closely that approximately one micrometer ($10^{-6}$ meter) of tissue separates them. The volume of the pulmonary capillary circulation is about 150 ml, but this is spread out over a surface area of approximately 750 sq feet. This capillary surface area surrounds 300 million air sacs called alveoli. There blood that is low in oxygen but high in carbon dioxide is in contact with the air that is high in oxygen and low in carbon dioxide for less than one second. This allows for the blood to be replenished with oxygen and for the excess carbon dioxide to be removed.

Hemoglobin, the iron-containing pigment of red blood cells, then carries the oxygen from the lungs to the tissues. In the lungs, hemoglobin combines readily with oxygen, by a process called oxygenation, to form a loose, unstable compound called oxyhemoglobin. In the tissues, where oxygen tension is low and carbon dioxide tension is high, oxyhemoglobin liberates its oxygen in exchange for carbon dioxide. The carbon dioxide then becomes carried by the blood serum to the lungs, where the whole oxygenation process begins again.

There have been numerous efforts in the past 40 years to achieve artificial lung function. Unfortunately, no new innovative respiratory assist therapy has been developed for patients with severe, life-threatening lung disease. This is largely due to inadequate knowledge of pulmonary pathophysiology, a lack of emerging therapies, and insufficient mechanisms for providing intermediate to long-term respiratory support. The lack of adequate technology for respiratory support for the patient with deteriorating lung function, in particular, has had profound effects on the quality of life for this increasingly large segment of the population.

The number of deaths annually from all lung disease is estimated to be approximately 250,000 (150,000 related to acute, potentially reversible respiratory failure and 100,000 related to chronic irreversible respiratory failure) with an estimated economic burden of disease in the range of 72 billion dollars per year. Furthermore, the emotional toll of progressive respiratory failure is profound, particularly as it affects children and adolescents with progressive pulmonary disease. The impact of this public health problem can be conceived in terms of the direct costs for intensive, sub-acute, and long-term health care services, and the indirect costs associated with lost wages and productivity for the patient and the patient's family, and the increased need for support services.

While the death rates for cardiovascular disease, cancer, and all other major diseases have recently decreased significantly, the rate of death related to chronic pulmonary lung disease (CPLD) has increased by 54%. Lung disease also represents one of the leading causes of infant mortality, accounting for 48% of all deaths under the age of one. For these patients, respiratory assistance during pulmonary failure has been achieved by employing ventilator therapy, despite the enormous cost and morbidity associated with this modality.

Furthermore, it is well accepted that closed, positive-pressure, mechanical ventilation, applied at moderate levels of intensity, for short periods of time, is a somewhat safe and efficient means for improving gas exchange in patients with acute respiratory failure. However, with prolonged duration of intensive respiratory support, serious adverse effects may occur. These effects, including oxygen toxicity, baromtrauma, altered hormone and enzyme systems, and impaired nutrition, may result in further injury to the failing lungs, or add significantly to the morbidity and mortality for these patients. As a result, alternative methods have been sought for augmenting blood gas exchange, where mechanical ventilation is inadequate or cannot be safely applied.

In view of the above and other reasons, there has been great interest in developing an artificial means for accomplishing physiological gas exchange directly to the circulating blood and bypassing the diseased lungs. While previous efforts have provided some measure of success, they have been limited in their usefulness or hindered by excessive cost.

One approach to artificial lung function has been by gas sparging or diffusion of gas across the membrane surface of hollow fibers placed within the blood supply. Previous efforts have achieved some success, and have taught much to pulmonary physiologists, but gas sparging or diffusion has yet achieved the degree of gas exchanges optimally desired.

Furthermore, other methods and artificial lung systems have been developed from introducing gaseous oxygen by air sparging. However, gas sparging is very detrimental to biological tissues such as red blood cells. Also, gas sparging attempts to control the differential pressure across thin gas/liquid membranes such as those found in porous-walled hollow fibers.

Another approach to artificial lung function, extracorporeal membrane oxygenation (ECMO), constitutes a mechanism for prolonged pulmonary bypass, which has been developed and optimized over several decades but has limited clinical utility today as a state-of-the-art artificial lung. The ECMO system includes an extra-corporeal pump and membrane system that performs a gas transfer across membranes. Despite the numerous advances in the implementation of ECMO over the years, its core technology is unchanged and continues to face important limitations. The limitations of ECMO include the requirement for a large and complex blood pump and oxygenator system; the necessity for a surgical procedure for cannulation; the need for systemic anticoagulation; a high rate of complications, including bleeding and infection; protein adsorption and platelet adhesion on the surface of oxygenator membranes; labor intensive implementation; and exceedingly high cost. As a result of these limitations, ECMO has become limited in its utility to select cases of neonatal respiratory failure, where reversibility is considered to be highly likely.

The development of the intravenous membrane oxygenation (IVOX) also represented a natural extension in the artificial lung art, since it was capable of performing intra-corporeal gas exchange across an array of hollow fiber membranes situated within the inferior vena cava but did not require any form of blood pump. The insertion of the IVOX effectively introduced a large amount of gas transfer surface area (up to 6000 cm$^2$) without alteration of systemic hemodynamics. Unfortunately, as with ECMO, the IVOX system has numerous limitations, including only a moderate rate of achievable gas exchange; difficulty in device deployment; a relatively high rate of adverse events; and a significant rate of device malfunctions, including blood-to-gas leaks due to broken hollow fibers.

A further approach to treat lung disease, is through the use of lung transplants. The improvement of methods to transplant viable lungs into patients is fundamentally the most significant recent advance in the therapy of chronic lung diseases. The most common indications for lung transplantation are emphysema, pulmonary fibrosis, cystic fibrosis, and pulmonary hypertension. Selection conditions emphasize the presence of irreversible disease localized to the respiratory system, and social and psychological conditions supportive of the ability to go through extended pulmonary rehabilitations. In contrast, the absence of these conditions present relative contraindications to this approach. The donor organ should originate in a relatively healthy, infection free individual, under the age of 65. Following these guidelines, success has been achieved in increasing numbers for patients throughout the United States.

Profound limitations in the number of donor organs has made this option unrealistic for the great majority of patients who would benefit the most. While rationing is the standard for all transplantable organs, the need for rationing is particularly acute in the case of the lungs, owing to the following issues: (1) the large discrepancy between donor and recipient numbers (3350 registration for lung transplant in 1999 and only 862 performed); (2) the relatively low yield of usable lungs, with only 5–10% of multiorgan donors yielding lungs acceptable for transplantation; and (3) the absence of effective temporary methods to support blood gas exchange during the waiting period prior to transplantation. The complexity of this problem is increased even further, when considering the inevitable compromise between supplying organs to patients who are the most ill, and who have the most to gain, but for whom outcomes are generally poor, versus relatively healthier patients with no complications, who have less need but for whom outcomes are predictably better. For example, a patient with emphysema is highly likely to achieve a positive outcome from transplantation, but generally will not exhibit improved survival. In contrast, a patient with cystic fibrosis has considerably higher risk of surgery due to the presence of multiorgan involvement of the disease, but for these young patients, successful transplantation optimizes survival.

Therefore, a serious need exists for new technology and therapeutic approaches that have the potential to provide intermediate to long-term respiratory support for patients suffering from severe pulmonary failure. Also, the need for an efficient and inexpensive technology to achieve sustained gas exchange in the blood, thereby bypassing the diseased lungs without resorting to chronic ventilation, remains paramount.

SUMMARY OF THE INVENTION

In one aspect, the present invention is directed to an photolytic artificial lung. It may be utilized for lung replacement and/or for oxygenation supplementation of the blood stream. It is particularly useful for treating a number of lung afflictions.

The photolytic artificial lung is a device, internal or external to the body, that utilizes light, such as a laser or lamp, to achieve physiological and therapeutic gas exchange in the blood stream. In such an exchange, oxygen is dissolved into the blood stream while carbon dioxide is removed and pH is controlled. This is due to the use of photochemistry. The photolytic artificial lung oxygenates blood without the deleterious effect on red blood cells associated with direct gas sparing (i.e. blood cell lysis, pH balance difficulties, etc.), while simultaneously controlling blood pH and carbon dioxide content.

More particularly, the photolytic artificial lung includes a photo-electro chemical cell (or "photolytic cell") that, in part, operates similar to the photosynthesis process that takes place in green plants. The photolytic artificial lung utilizes the photolytic cell to convert light energy in order to simultaneously generate oxygen from water, useful acidity and electrical energy. The photolytic cell also removes carbon dioxide from the blood stream. One or more photolytic cells can be included in the photolytic artificial lung of the present invention depending on the quantity, quality, etc. of desired gas exchange.

The light energy utilized in the present invention is ultraviolet ("UV") light or visible light, with the laser form being the most preferred. However, the light energy can also be broad-band, received by the way of a "light pipe" fiber optic cable or by the way of an attenuated total reflectance (ATR) link.

In the artificial lung, oxygen is generated from water present in the blood stream by means of the light dependent chemical reactions, photolysis and disproportionation. This is followed by the removal or clearing of carbon dioxide by the reactions of bicarbonate ion protonation and dehydration.

Photolysis is the initiation of a chemical reaction as a result of absorbing one or more quanta of radiation. Here, water is converted into oxygen by a light-activated catalyst, such as a semiconducting metal oxide. The metal oxide is utilized as a photo-absorbent material or a photo-absorption element. It is photolytically irradiated to form, from water present in the blood stream, hydrogen ions, hydrogen peroxide or other forms of oxygen gas precursor (active oxygen, "AO") and electrons by the absorption of one or more quantra of electromagnetic radiation. The free electrons generated are then electrically conducted away to avoid reversal of the reaction and optionally utilized to drive electrical devices, such as a pump.

For example, it has been found that active oxygen is readily generated in the present invention by the use of the anatase form of titania ($TiO_{2(a)}$) as the light absorbent material. The photo energy of light, such as ultraviolet laser light (about 350 nm), selectively excites $TiO_2$ semiconductor transition (about 350–390 nm band, or about 3.1 eV) with minimal material radiation or transmission. The ultraviolet energy produces charge separation in the anatase form of $TiO_2$, which then produces active oxygen (OA) and free electrons. The free electrons are then subsequently electrically conducted away due to the semi-conducting property of the anatase. Alternatively, other suitable light absorbent materials can also be utilized in the present invention at various wavelengths provided that the energy is sufficient to produce active oxygen.

Disproportionation is a chemical reaction in which a single compound serves as both oxidizing and reducing agent and is thereby converted into a more oxidized and a more reduced derivative. For example, hydrogen peroxide (active oxygen) produced during photolysis can be converted by means of manganese dioxide ($MgO_2$), or other catalytic agents and/or processes, into dissolved oxygen (DO) and water. This reaction produces dissolved oxygen (DO) from water and by-passes the harmful gaseous state.

Additionally, in the artificial lung of the present invention, carbon dioxide is removed from the blood stream by the means of the reactions of protonation and dehydration. In essence, the hydrogen ions formed during photolysis react with the bicarbonate ($HCO_3^-$) and carbonate ($CO_3^=$) ions present in the blood stream causing conversion of these ions into carbonic acid. In the presence of carbonic anhydrase, a blood component, the carbonic acid then quickly dissociates into water and carbon dioxide. The carbon dioxide gas is then subsequently vented into the environment.

Alternatively, due to concerns with infection in human lung assistance applications, a novel method and device is also disclosed herein for removing carbon dioxide from the system by molecular absorption. In this embodiment, carbon dioxide is removed from the blood stream by means of a carbon dioxide absorber device (i.e., a sorber), or other similar gaseous removal devices, under sterile conditions.

Consequently, the artificial lung of the present invention produces oxygen directly from water present in the blood stream, omitting the gaseous state which has previously caused pressure, shear, weight, and bulkiness problems with other blood oxygenation technologies. At the same time, the artificial lung also utilizes the hydrogen ions produced from the water to release the carbon dioxide. Additionally, the reactions occurring in the artificial lung do not involve the generation or use of high temperatures or pressures associated with previous devices and/or processes. The photolytic artificial lung is preferably designed to be self-contained and self-regulated. It requires no external gas supply.

A brief description of the pertinent reactions involved in the embodiment of the present invention utilizing anatase as the light absorbent material is provided below:

Photolysis

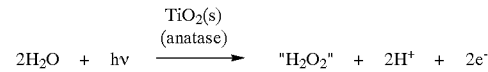

Disproportionation

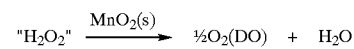

DO=dissolved oxygen in blood
Protonation ($H^+$ ions from photolysis reaction)

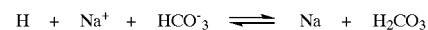

$CO_2$ Gas Generation

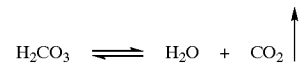

Catalyzed Dehydration (optional)

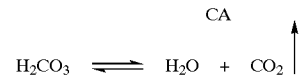

CA=carbonic anhydrase

The primary function of the photolytic artificial lung of the present invention is to provide respiration assistance in patients with lung disease, both in acute as well as chronic conditions. However, other medical applications are also feasible which also require the photochemical reactions of the present invention and/or the convenience of photolytic power. These include, among others, in-body drug level maintenance and release, and the contribution to the function of other organs such as the kidneys and the liver.

Additionally, the mix of products generated by the photolytic artificial lung of the invention, can be used in driving complex chemical processes, such as fermentations, and the regulation of drug levels. It can also be used to provide point-of-use chemicals such as hydrogen peroxide. The ability to produce electrical power can further be utilized in remote locations, and in powering small pumps (for example, it is contemplated that the electricity generated from the artificial lung can be used to drive an intravenously located blood pump, etc.). Parallel processes like oxidation and reduction can also be driven simultaneously at low then high (or visa versa) pH. The presence of fundamental oxygen and pH transformations can still further lead to many broad applications from sensors to industrial chemical processing, and as an energy source to remote sites.

In a more particular embodiment, the photolytic artificial lung of the present invention comprises an inlet for receiving blood from the blood stream of a patient. A pump extracts blood from the patient and moves the blood into at least one flow-through photolytic cell via the inlet. The photolytic cell contains a light-activated catalyst that converts water into oxygen, while at the same time removing carbon dioxide as described above. A light supply provides light energy to the photolytic cell. An outlet moves blood out of the photolytic artificial lung and back into a patient.

The photolytic cell is compatible with blood and provides high yields of oxygen to the blood stream. The resulting photolytic artificial lung is capable of use externally or internally by a patient, as well as in a stationary or portable form. Furthermore, the artificial lung is scalable to allow the photo-activated gas exchanges to be accomplished in a small and wearable extra-corporeal device, or in an intra-corporeal device inserted into a patient's venous blood supply.

In a further aspect, the present invention is also directed to a photolytic cell. The photolytic cell includes a transparent window. An anode is adjacent to the transparent window. A light-activated catalyst abuts the anode. A cell flow through area is adjacent to the light activated catalyst. A cation exchange membrane borders the cell flow through area. A catholyte abuts the cation exchange membrane. A cathode is present adjacent to the catholyte and is connected to the anode.

In another aspect, the present invention is further directed to a gas absorption or sorption device for collecting and converting a gas, such as carbon dioxide, to a solution or solid. The gas sorption device comprises a coalescence compartment including a gas head space and a coelesor connected thereto, wherein gas accumulates and/or is concentrated in the gas head space. A gas sorber connected to the coalescence compartment allows for the movement of gas from the gas head space to the gas sorber and the gas sorber converts gas to a solution or a solid. The sorber can be disposed or regenerated thereby avoiding the continuous venting of carbon dioxide to the atmosphere.

In an additional aspect, the present invention is further directed to a method for delivering oxygen to an aqueous bicarbonate ion solution. The method comprises moving the solution into a photolytic cell wherein light is utilized by a light-activated catalyst to produce oxygen from water, with a small concomitant pH change to cause a release of carbon dioxide; and moving the oxygenated solution out of the photolytic cell.

In still another aspect, the present invention is yet further directed to a method for oxygenating blood from a patient. The method includes moving deoxygenated blood into a photolytic cell; converting water to dissolved oxygen in the photolytic cell; binding dissolved oxygen to blood hemoglobin; forming carbon dioxide in the photolytic cell; removing carbon dioxide formed in the photolytic cell; and moving oxygenated blood out of the photolytic cell. This process emulates, to a certain degree, selected portions of the natural process by which plants produce oxygen, namely photosynthesis, and the way the lung eliminates carbon dioxide, namely through a pH drop. This method produces dissolved oxygen directly from water, omitting the gaseous state. It can be utilized to achieve therapeutic gas exchange in patients with respiratory failure.

These and other objects and features of the invention will be apparent from the detailed description set forth below.

BRIEF DESCRIPTION OF THE DRAWINGS

The present invention will become more fully understood from the detailed description given below and the accompanying drawings. The description and drawings are given by way of illustration only, and thus do not limit the present invention.

FIG. 2A shows a general illustration of the photolytic artificial lung connected externally to a patient. FIG. 2B shows an interior view of the components of one embodiment of the photolytic artificial lung. FIG. 2C also shows an inside view of an alternative embodiment of the photolytic artificial lung, and FIG. 2D illustrates the chemical reactions occurring therein.

DETAILED DESCRIPTION OF THE PREFERRED EMBODIMENTS

Figure 1:
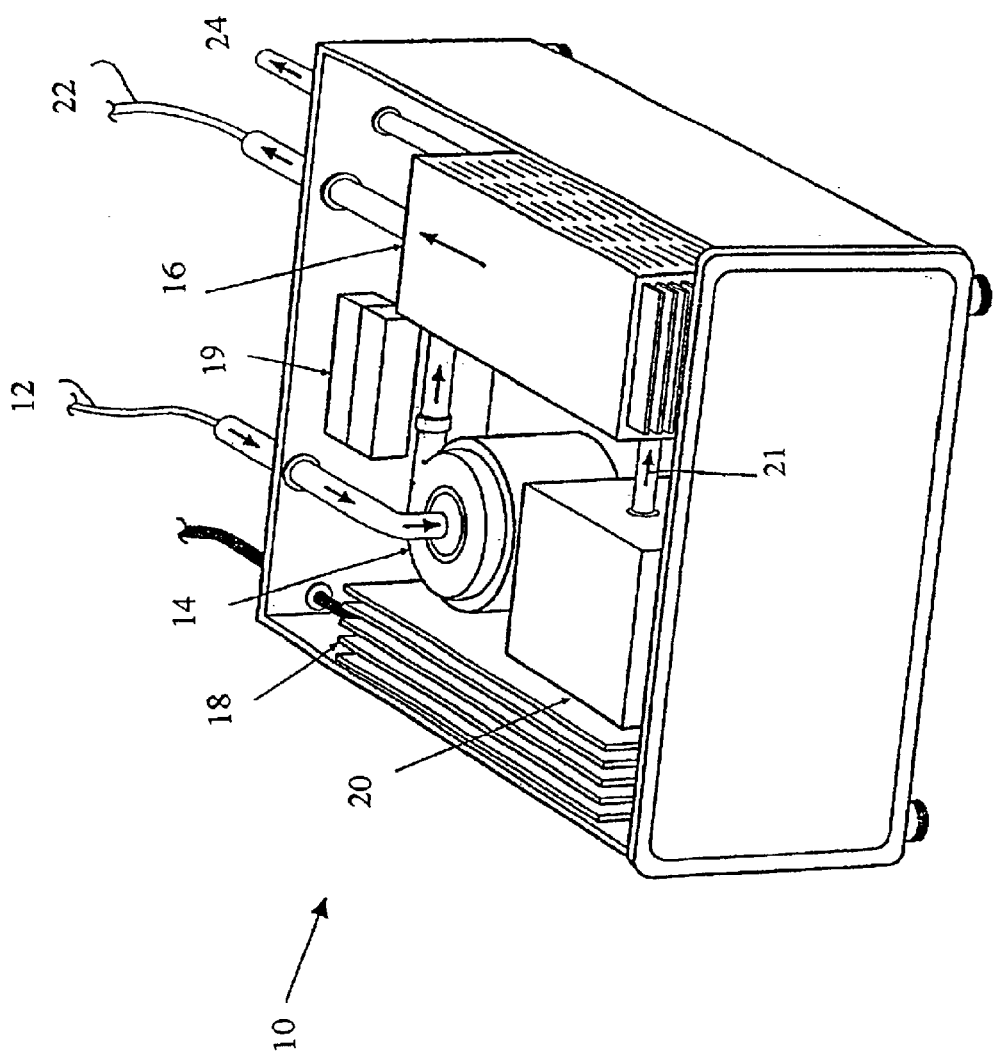
FIG. 1 shows a perspective view of an embodiment of a photolytic artificial lung designed for external or extra-corporeal usage.

The present invention is directed to a photolytic artificial lung having among other components, a photolytic cell. The photolytic cell is the fundamental functional unit of the invention. It acts as a general purpose oxygen generation, carbon dioxide remover and a pH controller. The photolytic cell includes a photochemically active material for use in producing various chemical reactions that enable the exchange of oxygen and carbon dioxide in the blood stream. By optimizing a relative balance between light activation, photolytic cell surface area and blood flow, it is designed to maximize efficient gas transfer. The photolytic cell, when used as a photolytic artificial lung application for lung replacement/supplementation, will oxygenate blood without the deleterious effect on red blood cells associated with direct gas sparing while simultaneously controlling blood pH and carbon dioxide contact.

Moreover, many devices other than an artificial lung can be derived and implemented based upon the photolytic cell. For example, the photolytic cell can be utilized to perform numerous operations including chemical processes, fermentation systems, regulation of drug levels, and replacement or assistance of one or more organ functions. Consequently, as a result of the somewhat similar photo-electrochemical transformations involved, the photolytic cell component of the invention can have additional applications outside of the artificial organ field.

In the preferred embodiment, the present invention is directed to the use of the photolytic cell in a novel respiratory assist device and process i.e., a photolytical artificial lung. The photolytic artificial lung includes one or more photolytic cells having photochemically active material and associated components for the production of oxygen, the regulation of pH, the removal of carbon dioxide, and the co-production of electrical power. The electrical power can be used to produce additional chemical changes or reactions. Optionally, the invention may include a photolytic chamber to house or hold a sufficient number of stacked or assembled photolytic cells to perform the rate of gas exchange desired.

The technology of the present invention is based in part, on the photo-initiated electrochemical transformation that mimics, to some degree, the natural process of photosynthesis. In photosynthesis, energy derived from sunlight is used to drive key metabolic reactions that fuel the growth of plants along with the production of oxygen.

The present photolytic artificial lung combines aspects of photosynthesis and the operations of the lung. In the lung, oxygen is transferred from the air to the blood as dissolved oxygen that is available for binding to hemoglobin (Hb) for transport to body tissues, and carbon dioxide is released from the blood into the air. The equilibrium shifts from the binding of dissolved oxygen to Hb and release of carbon dioxide are driven by gas pressure differences and carbonic anhydrous catalysis.

In the present invention, the photolytic artificial lung uses light energy to produce oxygen from water. Additionally, a concomitant small pH change causes a release of carbon dioxide from whole blood or serum. In the preferred embodiment, chemical materials formed in the chemical processes from the photolytic artificial lung are insoluble solids thereby preventing blood contamination.

Preferably, the photolytic artificial lung of the instant invention comprises a blood inlet cannula, a pump, at least one photolytic cell, a light source that irradiates the photolytic cells, an oxygenated blood outlet cannula and a carbon dioxide vent and/or absorption device. A power source and/or batteries can be present to power the pump or light source. One or more in-line sensors and processors can be present to monitor and optimize the flow through the system, the amount of oxygen and/or carbon dioxide generation, the presence of toxins, etc. Desaturated blood circulating through the device will be pumped through the photolytic cells where light activation will result in oxygen generation and ultimate carbon dioxide removal.

More particularly, FIG. 1 shows an embodiment of a photolytic artificial lung 10 developed as an extra-corporeal respiratory assist system. The artificial lung 10 includes a blood inlet 12 that cannulates blood from the patient into the artificial lung 10. The blood inlet 12 is connected to a pump 14 that draws blood from the patient into the artificial lung 10. The pump 14 directs desaturated blood through one or more photolytic cells 16 where light activation (for example, laser at 350–380 nm) results in oxygen generation and ultimate carbon dioxide removal via a carbon dioxide sorption device 24 or external ventilation. A power supply 18 or optional battery 19 activates the light source 20. The light source 20 emits light photos 21 which irradiate the photolytic cells 16. In turn, the photolytic cells 16 photochemically initiate a series of chemical reactions that produce oxygen and remove carbon dioxide from the blood. Oxygenated blood travels from the artificial lung 10 back to the patient by way of a blood outlet 22. Consequently, the artificial lung 10 takes blood from the venous circulation of a patient and returns it to the arterial circulation.

The present photolytic artificial lung omits the gaseous state that causes problems which have limited other blood oxygenation technologies, while consuming carbon dioxide. It also eliminates the need for an external oxygen source and minimizes the risk of inflammation produced by hollow fiber technology.

Also, the present photolytic artificial lung does not require the careful control of temperature or pressure. As briefly mentioned above, all materials for use in the present photolytic artificial lung remain as insoluble solids to prevent blood contamination. Blood contact with the coatings is minimized. Diffusion layers, which can decrease oxygenation rates, are minimized using electrical conduction of electrons and cations to and from the photolytic site, as is done in photosynthesis, by incorporating thin films having good photolytic transparency, and electrical and electrochemical conduction.

The wave length, beam size, pulse duration, frequency and fluency of the light source are adjusted to produce maximum and/or efficient gas exchange. Similarly, pump rate, flow-through capacity, etc. of the photolytic cells are also so adjusted. This is accomplished by sensors and regulators which also monitor reaction chemistry, toxins, etc. The sensors and regulators have the capacity to auto-regulate various parameters of the system in response to the conditions monitored by the sensors.

Most preferably, the photolytic artificial lung is designed to provide at least about 150 ml of dissolved oxygen per minute at 5 L/min of blood flow through the system for a human patient. Also, the components utilized for the photoactivated gas exchange are biocompatable.

The photolytic artificial lung can be designed so that it is an extra corporeal device or an intra-corporeal device. For example, the photolytic artificial lung can be designed as a miniaturized, implantable unit. Such a unit is configured to be implantable and it uses a transcutaneous energy transmission system and/or an internal light source for energy conversion.

Figure 2B:
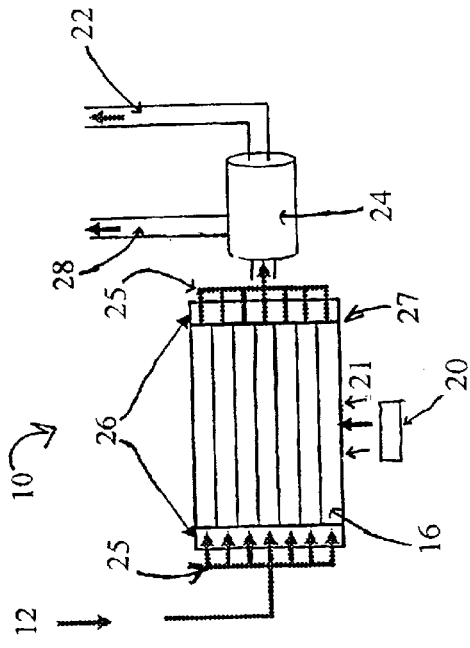
FIGS. 2A–2D illustrate the various embodiments of the photolytic artificial lung set forth in FIG. 1.
Figure 2A:
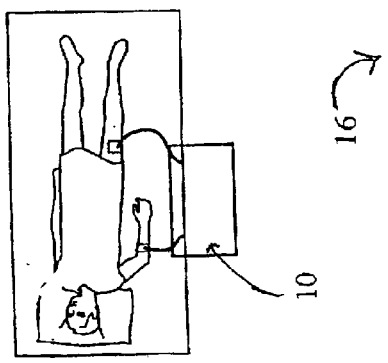
Figure 2C:
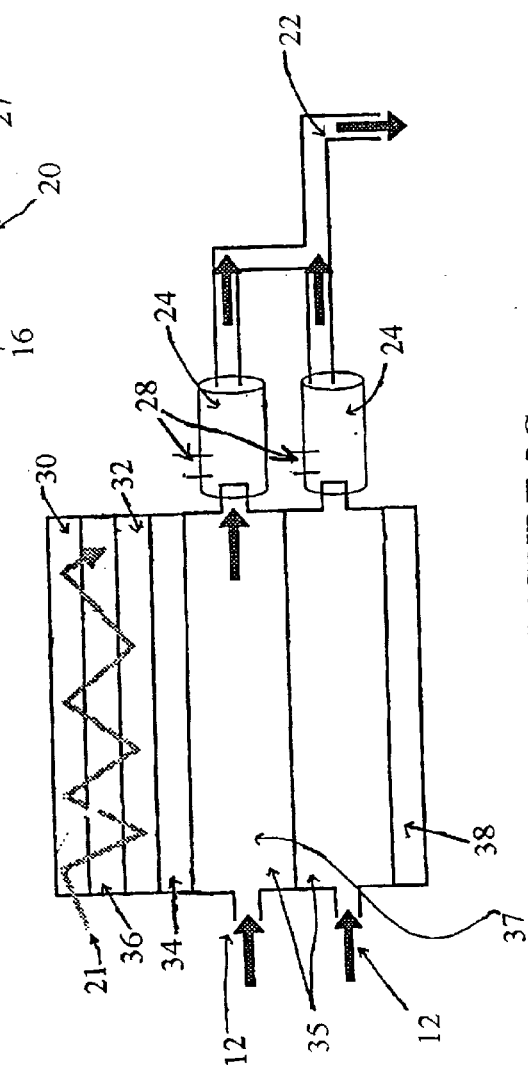
Figure 2D:
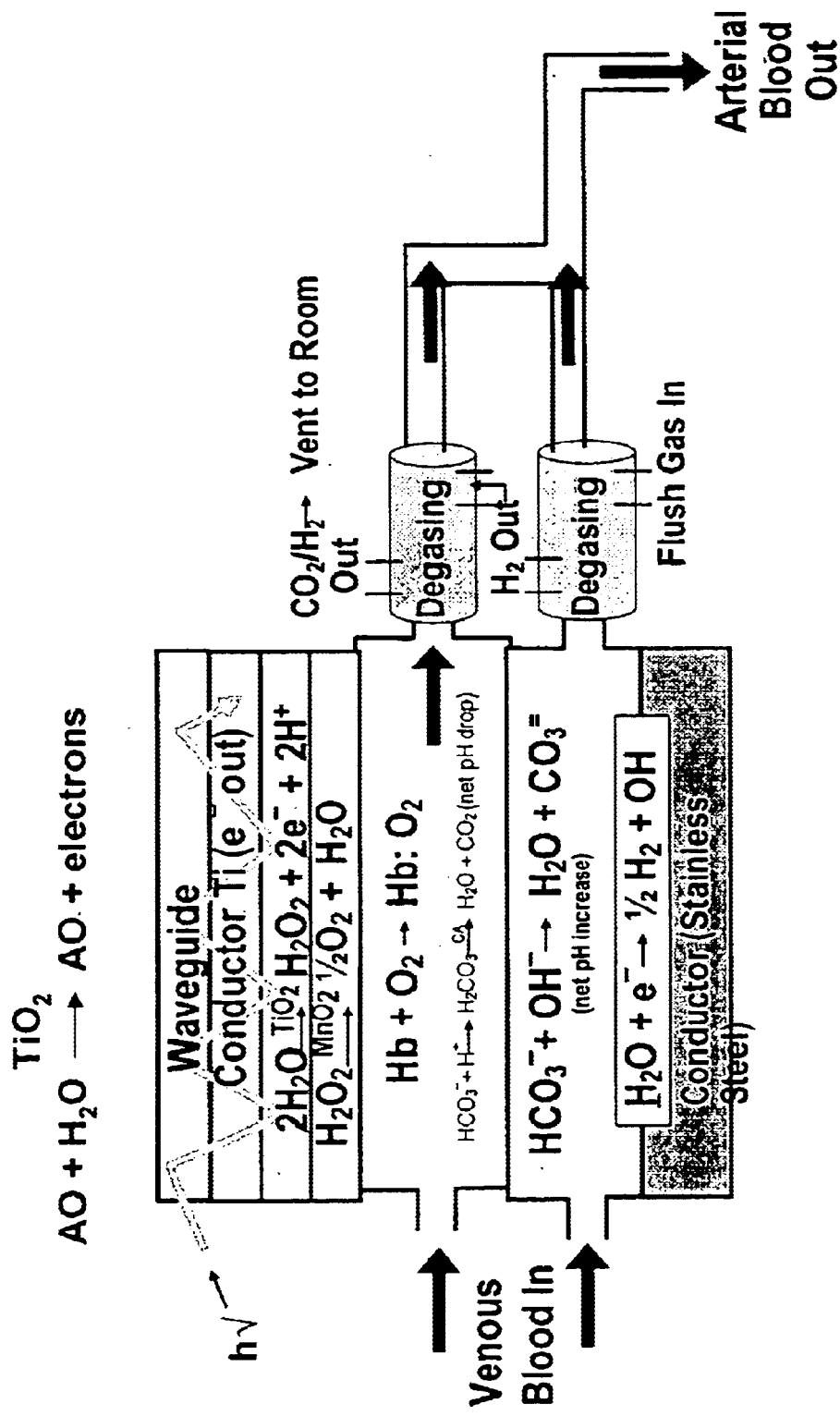

FIG. 2A shows a simple representation of a patient attached to a photolytic artificial lung 10 as an extra-corporal device. FIGS. 2B and 2C are enlargement views showing the components of various embodiments of the photolytic artificial lung 10. FIG. 2D shows the chemical transformations which occur in each compartment of the various embodiments of the artificial lung.

The photolytic artificial lung 10 pumps venous blood from the patient to the photolytic artificial lung 10 through a blood inlet 12. The venous blood enters by means of a flow distributor 25 into one or more photolytic cell(s) 16. The photolytic cell(s) may be optionally arranged to form a stack of photolysis cells 27. The amount of blood entering and leaving the photolytic cell(s) 16 is controlled by flow distributor 25. See FIG. 2B.

A light source 20 irradiates the photolytic cell(s) 16, thereby initiating the photochemical reactions within the photolytic cell(s) 16 that ultimately form dissolved oxygen that binds to blood hemoglobin (Hb). Excess carbon dioxide and hydrogen formed from the chemical reactions in the photolytic cell(s) 16 enter one or more gas sorption devices 24 for storage and/or eventual venting through a venting outlet 28. Once the blood has been oxygenated, and the carbon dioxide removed, the blood returns to the artery of a patient by way of blood outlet 22. Among the components of the photolytic artificial lung not illustrated in this embodiment is the blood pump, power supply, control electronics and sensory technology for monitoring reaction chemistry, the amount of oxygen, carbon dioxide, etc. generated the presence of potential toxins, etc.

The main component of the photolytic artificial lung is the photolytic cell 16. See, for example, FIG. 2C. Light energy 21 from a light source 20 enters the photolytic cell 16 through a transparent window 30 and activates a layer of light-activated catalyst 32. As discussed in more detail below, an example of such a light activated catalyst is anatase (TiO$_2$). Depending on the catalyst 32 used, the light-activated catalyst 32 converts water into intermediate active oxygen, hydrogen ions and excess electrons, or directly converts water into dissolved oxygen. An optional second catalyst 34 can be used to convert the intermediate active oxygen to dissolved oxygen, O$_2$. An example of such a second catalyst is manganese dioxide (MnO$_2$). Excess electrons are formed during the conversion of water to dissolved oxygen and are conducted out from the catalyst 32 to an anode conductor layer 36 such as gold or titanium metal film. In chamber 37, the dissolved oxygen binds to hemoglobin (Hb) in the blood and the oxygenated blood returns to the patient via an arterial blood outlet 22.

Additionally, in chamber 37, bicarbonate ions which are also present in the deoxygenated blood react with the hydrogen ions generated above to form carbonic acid. The carbonic acid is then converted to water and carbon dioxide by carbonic anhydrase. The water formed reacts with electrons at the cathode 38 to form hydrogen gas (H$_2$) and hydroxyl groups. The hemoglobin also releases carbon dioxide when the oxygen binds to the hemoglobin. The excess carbon dioxide and hydrogen created from the reactions occurring in the photolytic cell 16 enter one or more gas sorption devices 24 for storage or venting.

Figure 3:
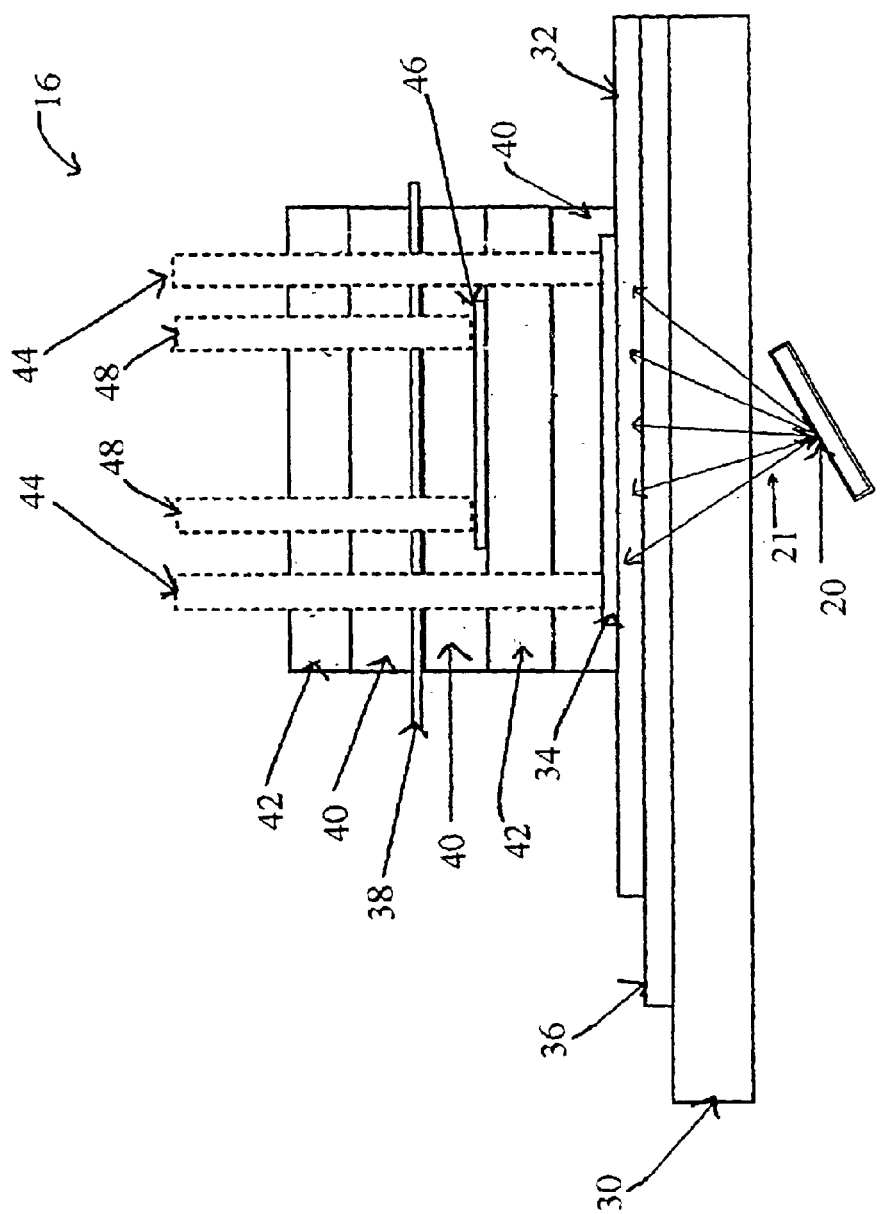
FIG. 3 shows a schematic view of the photolytic cell which was used to collect the laboratory data set forth herein.

FIG. 3 shows a flow-through embodiment of the photolytic cell 16. In the flow-through cell embodiment, the following main components of the photolytic cell 16 are assembled, i.e. a conductive coating of vacuum deposited Ti metal 36, a coating of adherent TiO$_2$ (anatase) 32, an optional MnO$_2$ particulate layer 34, and then tested using a bicarbonate solution. A UV laser light 20 was shown on the transparent glass or quartz substrate so to initiate the reactions. As discussed below, this cell was utilized to collect pH and data as a function of laser U.V. irradiation demonstrating the effectiveness of the invention.

In this regard, the photolytic cell 16 of FIG. 3 includes a transparent window 30 or wave guide for the entry of light energy in the form of photons 21 from a light source 20 such as an ultraviolet laser light. On one side of the glass slide is an anode conductor layer 36, such as titanium metal film. Attached to the anode conductor layer 36, is a layer of a light activated catalyst 32 such as anatase (TiO$_2$). An optional catalyst layer 34, such as manganese dioxide, is adjacent to the light activated catalyst layer 32. The photolytic cell 16 includes one or more layers of silicone gaskets or spacers 40 and an acrylic housing 42. A pair of anolytes 44 (in/out) are connected to the light activated catalyst layer 32 or optional catalyst layer 34 and extend through the photolytic cell 16 away from the transparent window 30. The photolytic cell 16 further includes a cation exchange member 46, such as a NAFION® membrane. A pair of catholytes 48 (in/out) are connected to the cation exchange member 46 and extend outwardly through the photolytic cell 16 generally away from the transparent window 30. The photolytic cell 16 further includes a cathode layer 38, such as Pt foil, adjacent to the cation exchange member 46. The operation and use of this embodiment of the invention is more particularly described in the Examples below.

Figure 4:
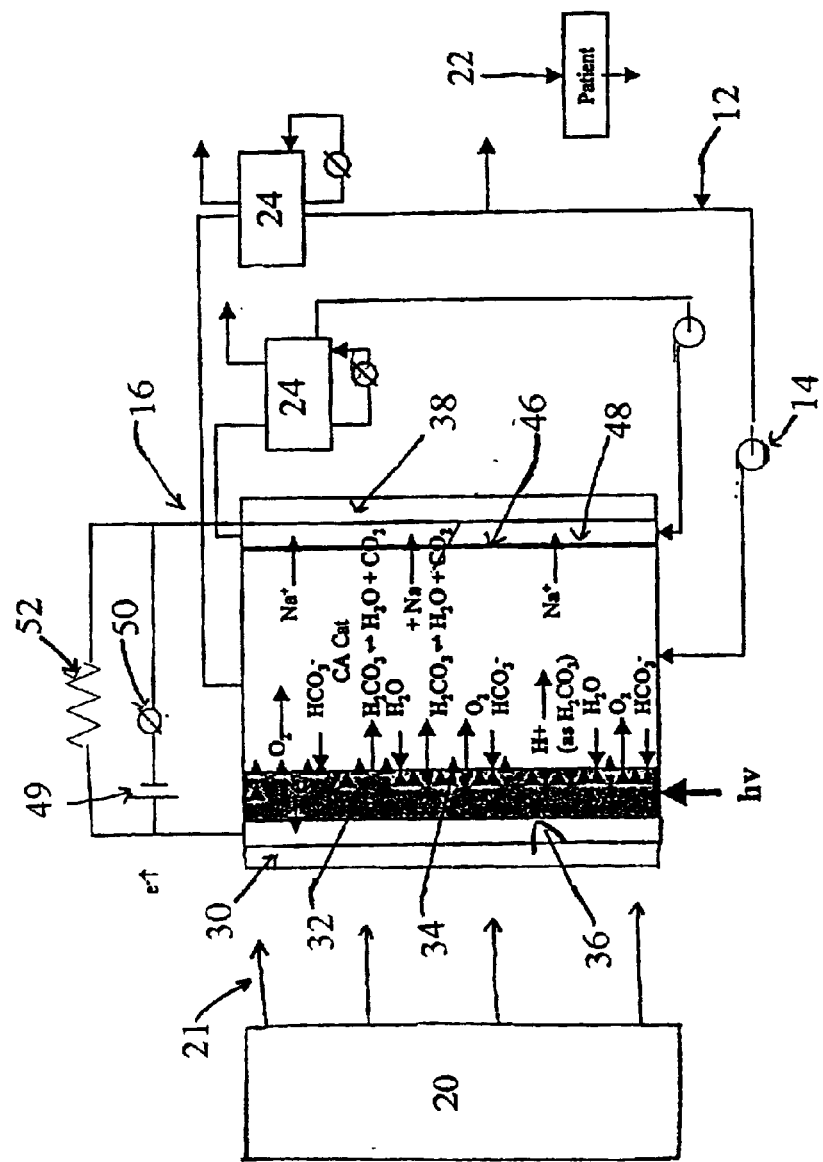
FIG. 4 shows an overall schematic diagram of the preferred embodiment of the photolytic artificial lung of the present invention.

FIG. 4 is a schematic drawing showing the electrical and chemical transformations which occur in the photolytic cell 16 of the photolytic artificial lung 10. Venous blood (low in oxygen and high in carbon dioxide) from a patient enters the photolytic cell 16 through inlet 12 by way of a peristaltic pump 14. Light photons (hv) 21 generated by light source 20 enter through a transparent window 30 or waveguide and activate the light activated catalyst 32 such as 100 µm TiO$_2$ (anatase). The light activated catalyst 32 either directly converts water to dissolved oxygen or converts water to active oxygen and hydrogen ions and an optional second catalyst 34, such as maganase dioxide (MgO$_2$) on a porous film, converts active oxygen (e.g. H$_2$O$_2$) into dissolved oxygen (DO). The dissolved oxygen then binds to hemoglobin present in the blood.

The electrons released from the conversion of water to oxygen are collected in the collector electron anode 36. An electrical current formed from a battery 49 allows the electrons to flow from the anode 36 to the cathode 38, such as graphite or nickel, so that the electrons do not react with the active oxygen to cause a back reaction and the reformation of water.

The electrical current and electron flow can be regulated by a current regulator 50 or resistor 52. The electrons can react with water to form hydrogen gas, H$_2$, and a hydroxyl ion (OH$^-$). The hydrogen gas formed is moved to a gas sorption device, where it is stored and/or released (i.e., expired). Sodium (Na$^+$) ions from the blood migrate across the cation exchange membrane 46 and react with hydroxyl ions to form sodium hydroxide (NaOH) in the catholyte 48. The hydrogen ions formed from the conversion of water at the light activated catalyst reacts with bicarbonate ions to form carbonic acid, which is converted by carbonic anhydrase enzyme present in the blood or added to form carbon dioxide and water. The carbon dioxide formed in the photolytic cell 16 along with the carbon dioxide released from the blood is moved to one or more gas sorption devices 24 or vented. The oxygenated blood exits the photolytic cell 16 via an outlet 22 and returns to the artery of the patient.

The various particular components and/or processes of the present invention are described in more detail below:

1. Transparent Window 30

The transparent window 30 can be formed from glass, quartz slides, quartz, etc. Glass is useful in forming the transparent window provided that the UV transparency is adequate at the wavelength needed. Quartz slides are also useful because of its high UV transparency. For the transparent window, light entry into and through the transparent window can be from the back, side, or bottom. Edge illumination through the transparent window can optionally include a lens or wave guide.

The transparent window can further include a wave guide. A wave guide uniformly distributes photons (hv) from the light over the surface of the light activated catalyst. Particularly, the wave guide causes the light photons to travel in a path so that the photons maximally contact the entire layer of the light activated catalyst. Light enters the wave guide in the side of the transparent window generally parallel to the surface of the light activated catalyst that is attached to the transparent window. The wave guide allows for maximal light photon contact with the light activated catalyst without directly illuminating the side of the entire light activated catalyst attached to the transparent window. The wave guide also allows form maximal photolytic cell staking because light is not required to directly illuminate the light activated catalyst but rather can be indirectly illuminated by side or edge entry in the transparent window. The wave guide provides additional efficiency to light used in the photolytic cell because the light can be spread across the entire surface of the light activated catalyst.

2. Anode Conductor Layer 36

The anode conductor layer 36 conducts electrons formed from the reaction of water to oxygen out of the anode. The anode conductor layer prevents the electrons from reacting back with the oxygen to reform water, thereby allowing maximal formation of oxygen. The anode conductor layer is applied or attached to at least one side of the transparent window.

The anode conductor layer can be formed at least two different ways. The anode layer can be formed by attaching a thin film of uniform metallic conductor to the transparent window using vapor deposition. The film preferably has a thickness of less than about 0.2 µm. Preferably, the film is formed from gold or titanium. Gold remains metallic at all conditions but can be very efficient at UV light blockage or reflection. Titanium can be oxidized to $TiO_2$ by adding $O_2$ to the deposition chamber to yield a possible catalyst layer with excellent adhesion.

The anode conductor layer 36 can also be formed by using photo-resist technology. Under photo-resist technology, grids are prepared with masks using vapor deposition. Conductor line spacing, width and thickness optimization may be required to prevent excessive attenuation, and provide sufficiently close conductive areas to sweep electrons away from the light activated catalyst layer.

3. Catalysts 32 and 34

A light activated catalyst 32 is coated onto the anode conductor layer. The light activated catalyst is photochemically activated and reacts with water to form dissolved oxygen or a free radical oxygen intermediate that is ultimately converted to dissolved oxygen. The term active oxygen in the present application defines any free radical oxygen intermediate formed in the photolytically catalyzed reaction of water that is ultimately converted to dissolved oxygen. The active oxygen formed is in the form of a peroxide, such as hydrogen peroxide, $H_2O_2$, or peroxide ion salt, hydroxyl free radical, super oxide ion, etc., and is converted into dissolved oxygen in the presence of a catalyst. The active oxygen formed depends on the light activated catalyst used. Also, depending on the light activated catalyst used, water may be photolytically converted directly into dissolved oxygen without first forming an active oxygen.

Several different catalysts can be employed for producing dissolved oxygen photochemically. One catalyst that can be used to photochemically produce oxygen is zinc oxide. By using zinc oxide, peroxide ($H_2O_2$) is produced directly from water at blood pH. $H_2O_2$ is an excellent form of active oxygen for providing sufficient potential diffusion distance, and also for the disproportionate reaction to dissolved oxygen and water via a solid $MnO_2$ catalyst (similar to green plant $O_2$ generation site) occurring photochemically at <340 nm by way of metal ion assisted disproportionation with catalase and other hydroperoxidases. Zinc oxide film has other positive attributes including, known film formation technology (e.g. via the zinc/nitrate/glycine reaction), low toxicity concerns, and low cost.

An additional catalyst that can be used to photochemically produce dissolved oxygen is tungstate ($WO_3$) that is exposed to visible light and using $e^-_{scb}$ removal. $WO_3$ yields oxygen ($O_2$) directly from water without the need to first produce an active oxygen species. Oxygen is generated stoichiometrically and the "back reaction" is unfavored so that there is not significant competition to the direct formation of dissolved oxygen. Only visible light is needed to generate dissolved oxygen from $WO_3$, no more than about 496 nm. $WO_3$ films present low toxicity concerns. Preferably, the use of $WO_3$ further includes the removal of excess $e^-_{scb}$ formed during oxygen formation from water.

Another catalyst suitable for reacting with water is $TiO_2$ (anatase) irradiation with, followed by dissolved oxygen production at a metal catalyst, such as a $MnO_2$ catalyst, or other similar catalyst. $TiO_2$ removes the $e^-_{scb}$ efficiently from the production area in order to ultimately obtain good dissolved oxygen production and minimize any back reaction to reform reactants. The removal of $e^-_{scb}$ is performed through conduction via the semi-conductor property of the $TiO_{2(a)}$ with enhancement via application of a small DC bias voltage. $TiO_2$ irradiation also presents low toxicity concerns. $TiO_2$ provides very high insolubility and kinetic inertness to minimize dissolution and fouling during use and maintenance. Preferably, UV light is chopped or pulsed during $TiO_2$ irradiation to allow time for the chemical reactions to occur since with continuous irradiation causes the $e^-_{scb}$ to accumulate and force a back reaction to form water. A pause in the irradiation allows time for the slower, but still extremely fast irradiation in the range of µsec to msec to occur to occur.

A further catalyst for reacting with water to ultimately form dissolved oxygen is a semiconductor powder (SCP)-filled UV/VIS light transparent thermoplastic film. SCP-filled thermoplastic film is relatively inexpensive to manufacture and form into shape. SCP film is easily moldable, extrudable, cut and machined. SCP can be used very efficiently in surface applied only form. Also, SCP has low toxicity concerns. Optimized commercial products (conductive plastic filler powders) are available with good properties for dispersion, particle-to-particle electrical conductivity (for $e^-_{scb}$ removal), and resistance to sloughing off that can be used with the present photolytic artificial lung.

The following additional preferred conditions may be used for each of the above-mentioned catalysts. First, an application of a small (e.g. up to a few volts DC) bias voltage can be applied to help ensure that the $e^-_{sch}$ is quickly conducted away from the production site. Second, a chopped illumination, instead of a continuously applied illumination, may allow secondary chemical reactions to occur since the secondary chemical reactions are slower than the photochemical reactions and enhance photo yields by allowing the excited electrons to exit the system and not be present for regeneration of starting material, i.e., water.

Of the above-mentioned catalysts, the $TiO_2$ (anatase) catalyst followed by a second metal catalyst is the most preferred. When the $TiO_2$ catalyst is used, the light-titania interaction is the first step in the ultimate formation of dissolved oxygen. It is known that surface hydrated particulate $TiO_2$ (anatase) solid, $TiO_{2(a)}$—$OH_2$ or $Ti^{IV}O_{2(a)}$—$OH$, is an efficient UV light (hv) acceptor at wave lengths <390 nm, resulting in active oxygen formation from sorbed water and hydroxyl groups. The most probable reaction is believed to be:

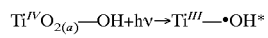

$$Ti^{IV}O_{2(a)}-OH + hv \rightarrow Ti^{III}-\cdot OH^*$$

It is noted that other bonds to Ti have been omitted for clarity. The reactant and product of the above reaction are solid materials. In the above reaction, $H_2O$ is already bonded to the surface of the $TiO_{2(a)}$ catalyst as $H_2O$ or as hydroxyl ion ($OH^-$), i.e. $Ti^{IV}O_{2(a)}$—$OH_2$ or $Ti^{IV}O_{2(a)}$—$OH$, respectfully. Hence, no atoms are required to move during the very fast photon absorption process. The * represents a low lying excited electronic state where the energy of the photon is used to transition or excite an electron from a nonbonding orbital on the oxygen to a molecular orbital centered on the titanium ion, hence converting the titanium into a trivalent oxidation state. The molecular orbital centered on the titanium ion is known to be a part of the semiconduction band ("scb"), and so the electron is readily conducted away from the site to form a bipolar charged grain, or, if connected to a closed DC electrical circuit, resulting in full charge separation, i.e.,

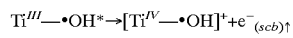

$$Ti^{III}-\cdot OH^* \rightarrow [Ti^{IV}-\cdot OH]^+ + e^-_{(scb)}\uparrow$$

If the $e^-_{scb}$ is not conducted away or otherwise removed by reaction with an oxidant present in the solution, the $e^-_{scb}$ could react with the hydroxyl free radical and reverse or back react so that the system would return to its original state and form water. In this latter case there would be no net reaction and the photolytic energy will appear as a small amount of heat. Hence the charge separation process and removal of $e^-_{scb}$ is considered an important first step of the photolytic cell dissolved oxygen generation process.

The hydroxyl free radical (·OH) group present is used to represent the initial form of the active oxygen generated by the photolytic process. It is not certain that .OH is the dominant species present when $TiO_{2(a)}$ is photolyzed. The active oxygen formed could generally be in the form of a superoxide, hydrogen peroxide, or a hydroxyl free radical. However, the form of this active oxygen produced has sufficient thermodynamic driving force to form active oxygen from water. For the $TiO_{2(a)}$ catalyst at neutral pH, these highly reactive hydroxyl free radicals either back react as described above, or rapidly dimerize to form ($\mu$-peroxo) titanium (IV) and hydrogen ions, i.e.

These $H^+$ ions are valuable for blood-$CO_2$ level control. The rate of dissolved oxygen production is the rate at which the active oxygen splits out to form $O_{2(aq)}$ and reforms $TiO_{2(a)}$, i.e.

$Ti^{IV}-O-O-Ti^{IV} \rightarrow Ti^{IV}-O-Ti^{IV}+\frac{1}{2}O_{2(aq)}$ (as dissolved oxygen)

In an unwanted but unharmful second side reaction, any $O_{2(aq)}$ produced can react with $e^-_{scb}$ previously produced but not yet conducted away. These $e^-_{scb}$ negative charges tend to reside on the surfaces of the $TiO_2$ particles so that the negative charge are most separated. Therefore, these $e^-_{scb}$ electrons are available for reduction reactions with $O_2$ or the $\mu$-peroxide linkage to produce species such as $O_2^-$, $O^=$, $O^-$, etc., thereby decreasing dissolved oxygen yields. In order to minimize side reaction, the illumination is pulsed instead of continuous. The delay caused by illumination pulsation allows the $e^-_{scb}$ to be conducted away in one direction and the dissolved oxygen to diffuse away in another (E. Pelizzetti, M. Barbeni, E. Pramauro, W. Erbs, E. Borgarello, M. A. Jamieson, and N. Serpone, *Quimica Nova (Brazil)*, 288 (1985)). Also, illumination pulsation prevents the local populations of $O_{2(aq)}$ and $e^-_{scb}$ from becoming so high that reaction between them becomes fast. The pulse rates involved are extremely short in the $\mu$sec-msec range so that there is little effect on $O_{2(aq)}$ production rates. Enhanced yields are also possible for photolytically established charge separation when a bias voltage is present across the coating. (X. Z. Li, H. L. Liu, and P. T. Yue, *Envison-Sci-Technology*, 2000, 34, 4401–4406.) A small bias voltage may also be used to further reduce the amount of $e^-_{scb}$ present and produce more dissolved oxygen.

Another way to increase the amount of dissolved oxygen production in the $TiO_{2(a)}$ system is to provide a means to speed the rate of release of the trapped $\mu$-peroxide as hydrogen peroxide as to active oxygen.

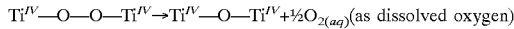

$H_2O_2$ is an excellent form for the active oxygen species as it readily migrates and is easily catalyzed to disproportionate into dissolved oxygen and water.

Stable free radicals (SFRs) can be used to release the trapped $\mu$-peroxide as hydrogen peroxide. SFRs can exist as free radicals for extended periods of time relative to the hydroxyl free radical. SFRs have been found useful for promoting electron transfer reactions. They electronically and reversibly rearrange into reduced or oxidized species one electron at a time as set by the reaction conditions. Biological systems are known to use SFRs as respiratory carriers, such as quinone coenzymes including ubiquinone, vitamin K, etc. The SFR shuttles the reactivity from the point of generation to the point of $H_2O_2$ production, or even directly to the metal ion $MnO_2$ catalyst for dissolved oxygen production. Components found in biological systems such as vitamins E, C, K, etc. also may function in the role of SFRs except without recycle. At least four classes of SFRs exist from which a suitable agent can be selected: hindered hydroxylated aromatics (quinones, substituted phenolics); organic peroxide precursors (alcohols, etc.); peracid precursors (acylating agents, etc.); and nitroxides, $RN \rightarrow O$.

Therefore, for the $TiO_{2(a)}$ photocatalyst to be useful, a means for releasing the $\mu$-peroxide energy is needed, such as soluble $H_2O_2$, since $H_2O_2$ can diffuse to the $MnO_2$ for dissolved oxygen production, or by conducting the oxidizing power to another active oxygen form, such as SFRs in the adjacent solution that can be used in dissolved oxygen production, or using the $Ti^{IV}-O-O-Ti^{IV}$ content to electronically remove electrons from the $MnO_2$ cluster/particle (as is done in green plant photosynthesis by the "D" protein). In the last means, only an electron flows from the water through the $MnO_2$ to the $\mu$-peroxo linkage through delocalized bonds. This electron replaces the $e^-$ lost from the $TiO_{2(a)}-OH$ system as $e^-_{scb}$.

The formation of $H_2O_2$ as the active oxygen is valuable since $H_2O_2$ can be rapidly converted to dissolved oxygen in 100% yield using many different methods: thermally; metal ion catalysis; particulate/surface catalysis; base catalysis; and free radical reaction with reductant initiation. Preferably, metal ion catalysis, such as, $MnO_{2(s)}$, provides an efficient catalyst for $H_2O_2$ disproportionation to water and $O_2$, on thin film substrate constructs.

Photo catalyst systems such as zinc oxide, ZnO, release peroxide as the active oxygen more readily than does $TiO_2$. Less acidic metal ions under the Lewis acid/base theory definition cannot sufficiently stabilize the highly alkaline peroxide ion relative to water protonation ($pK_{a1}$ of $H_2O_2$ is 11.38 (25° C.)) to form it within the solid phase, and so hydrogen peroxide, $H_2O_2$, is readily formed from ZnO:

ZnO films and particles can be prepared in a number of ways with varying but controlled composition, morphology and porosity. For example, mirrors of zinc, doped zinc, and zinc alloys and can be sputtered down onto an optically transparent support, followed by oxidation with $O_{2(g)}$. This treatment produces a metal/metal oxide (Zn/ZnO) film. Another highly effective approach to semiconducting ZnO-based films is to utilize a process for optical glass coatings. (L. R. Pederson, L. A. Chick, and G. J. Exarhos, U.S. Pat. No. 4,880,772 (1989).) The optical glass coating technique is based on applying a zinc nitrate/glycine aqueous solution as a dip or spray, followed by drying (110° C. for 15 min), then heating (450–500° C. for 3 min) to initiate a self-oxidation reaction during which the carbon and nitrogen exits as gases leaving an adherent yet porous film bonded to the underlying surface (e.g. glass) and is referred to as the glycine nitrate process. (L. R. Pederson, L. A. Chick, and G. J. Exarhos, U.S. Pat. No. 4,880,772 (1989).) The ZnO film is normally produced doped with alumina by including aluminum nitrate in the aqueous formulation for the initial dip. Many other metal ion blends are also possible with this technique.

Tungstate only requires visible light to produce dissolved oxygen, and produces dissolved oxygen directly without requiring a second catalyst to form dissolved oxygen. The lower photon energy requirement for $WO_3$ is due to the smaller band gap of 2.5 eV versus at least 3 eV for $TiO_{2(a)}$. As with the $TiO_2$ anatase system, high yields are possible with the $WO_3$ catalyst if the $e^-_{scb}$ is removed. The production of $O_2$ increases very significantly if $RuO_2$ (ruthenium oxide) is placed on the surface of the $WO_3$. This is consistent with the fact that $RuO_2$ is a known good catalyst for $O_2$ production and so represents a route to improving other approaches.

An advantage may exist if the dissolved oxygen producing film could be a filled plastic. Such materials are often inexpensive and manufactured easily. Commercial sources exist for semi-conducting, low light absorbing, inorganic fillers for plastics which are supplied in ready made condition for incorporation into plastics, making the plastics electrically conductive. For example, E.I. duPont Nemours, Inc. sells electroconductive powders (EPC) under the trade name ZELEC® ECP for such purposes. The conductive substance in ZELEC® ECP is antimony-doped tin oxide ($SnO_2$:Sb). The bulk of these materials, onto which the conductor is coated, are familiar inorganics such as mica flakes, $TiO_2$, and hollow silica shells, or ECP-M, ECP-T and ECP-S respectively. Pure $SnO_2$:Sb-based material is designated ECP-XC and is a much smaller particle than the other materials. About 25–45% by weight of the ECP products are used so that the particles are sufficiently close to each other to provide internal electrical connections throughout the otherwise non-conducting plastic. ECP-S and ECP-M normally perform best for lower concentrations. Thin films of ECP-XC can provide an attractive coating because they are very fine grained and strongly light absorbing.

The $TiO_2$ layer can be formed a variety of ways. The $TiO_2$ layer can be formed by sol gel, drying and baking. A product under the trademark LIQUICOAT® from Merck & Co., Inc., which hydrolyzes $Ti(OR)_4$ type material in water to form $TiO_2$ and 4ROH can be used to form the $TiO_2$ layer under a sol gel/drying/baking process. $TiO_2$ can also be formed from preparing an anatase suspension from dry powder, then dipping, drying, and baking the suspension to form the $TiO_2$ layer. Another way the $TiO_2$ layer can be formed is by e-beam evaporating titanium and subsequently exposing the titanium to $O_2$ within a deposition chamber. The $TiO_2$ layer can also be formed by adding titanium salt to water and adjusting the pH to ~2–7 to form a suspension, then dipping the suspension and allowing the suspension to dry.

Active oxygen is created from $TiO_2$ by irradiation with UV light, but the chemical form of the active oxygen is very reactive and can be lost by side reaction occurring in close proximity to the $TiO_2$ particle surface where active oxygen is generated. There are at least three ways to minimize the loss of active oxygen to unwanted side reaction: 1) move the active oxygen to dissolved oxygen conversion point closer to the active oxygen generation point, i.e. move the metal ion catalyst as close as possible to the $TiO_2$, which may require intimate contact between these two materials, in the order of angstroms; 2) electrically connect the two points, as is done in photosynthesis by a protein capable of conducting electrons; or 3) convert the active oxygen into a longer lived intermediate active oxygen species that has time to migrate to more distant $MnO_2$ centers for conversion to dissolved oxygen.

The amount of active oxygen lost by side reactions can be minimized by introducing an active oxygen carrier molecule into the media, or "D," by analogy to a photosynthetic system. Agents for use with species D can be selected from two groups, those that readily form organic peroxides, and those that form "stable" (i.e. long-lived) free radicals. Organic peroxides are useful because they easily produce dissolved oxygen when contacting $MnO_2$, and readily form by oxygen insertion. The organic peroxide reactions are as follows:

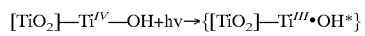

where the excited electronic state corresponds to the ligand-to-metal charge transfer (free radical pair), and is followed by the reaction:

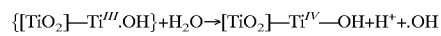

where conduction of the $e^-$ into the semiconductor conduction band and away from the side of the particle near the .OH prevents recombination of that $e^-$. As shown in the reaction above, the $TiO_2$ anatase is regenerated. The above reaction produces a hydrogen ion for eventual $CO_2$ removal. Also, the active oxygen produced in the above reaction is in close proximity to $TiO_2$ as a free radical hydroxyl groups, .OH.

As .OH is extremely reactive, lasts only for a very short time and does not diffuse far. One way to increase the amount of time that .OH is present is by introducing a species that stabilizes the *OH. Similar to photosynthesis, a species "D" is introduced into the test system to capture the hydroxyl free radical in a longer lived species. The species D is generally shown the in following chemical reaction:

where D can be RC(O)OH:

or D can be $R_3COH$:

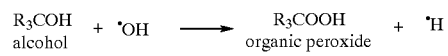

or D can be a free radical scavenger that forms a stable free radical:

or D can be 2,6-di-tertbutyl phenol:

t-Bu-Ar—OH+.OH→t-Bu-Ar—O.+H$_2$O

The 2,6-di-tertbutyl phenol is the most desired D species, as a strongly reducing .H radical is not formed that would consume OH$^-$ and [TiO$_2$]—Ti$^{III}$ in wasteful reactions, regenerate the starting materials, and result in a low photochemical yield.

The catalyst used to convert active oxygen into dissolved oxygen includes metal ions capable of redox cycling, such as Fe$^{II}$, Fe$^{III}$, Cu$^{I}$, Cu$^{II}$, Co$^{II}$, Co$^{III}$, Mn$^{II}$, Mn$^{III}$, Mn$^{IV}$, etc., or metal oxides formed from metal ions capable of redox cycling, such as manganese dioxide, MnO$_2$. The present reaction produces dissolved oxygen directly from water and by-passes the gaseous state. The MnO$_2$ catalyst is most preferred because it forms dissolved oxygen efficiently and is not highly selective of the active oxygen form.

One way to facilitate the conversion of active oxygen to O$_2$ is by doping the surface of the TiO$_2$ anatase with manganese (Mn). Surface doping the TiO$_2$ with Mn provides a highly productive active oxygen to O$_2$ conversion catalyst. Active oxygen disproportionation is rapid when dropped on a Mn-doped anatase. Alternatively, active oxygen can also be converted to O$_2$ by placing MnO$_2$ on the surface of the anatase in conductive form. In this form, electrons are catalytically passed from water to the active oxygen region of the anatase. Such an arrangement more closely mimics photosynthesis O$_2$ production.

Another way to convert active oxygen to O$_2$ in the photolytic cell is by using a MnO$_2$ octahedral molecular sieve (MOMS) material as the dissolved oxygen catalyst. The MOMS material has an open gel-like structure and is closely related to zeolites in structure. The MOMS material is easily formed from manganese salts through precipitation and drying.

Active oxygen may also be converted to O$_2$ in the photolytic cell by a superoxide dismutase (SOD) catalyst. SOD catalyst is already available in the human body and can provide the required conversion of active oxygen, e.g. as O$_2^-$, into a dissolved oxygen precursor, i.e. H$_2$O$_2$, to supplement the photolytic cell and Mn-doped anatase.

Blood is routinely exposed to active oxygen forms and blood already has built-in measures for self protection against low levels of excessive active oxygen. ("Inorganic Biochemistry", G. L. Eichhorn (Ed)., Chap. 28, p 988 (Elsevier, Scientific Publ., NY (1975), and "Advances in Inorganic and Bioinorganic Mechanisms", A. G. Skes (Ed), p 128 (1986) (Academy Press, NY)) Active oxygen forms within the body in the form of species such as peroxides (R—O—O—H) and superoxide (O$_2^-{}_{(aq)}$), which are disproportionated to dissolved oxygen and H$_2$O respectively by hydroperoxidases, such as catalase which contains zinc ion, peroxidase which contains iron ion, etc., and superoxide dismutase metal ion-based enzymes, such as ferriprotophyrin IX. Alternatively, these enzymes can utilize active oxygen forms to oxidize a wide range of chemical reductants such as ascorbic acid and other vitamins such as such as vitamin E and vitamin K. Although the photolytic artificial lung does not rely on such protection mechanisms, it is noteworthy that low levels of such molecules are not new to body chemistry and that conventional mechanisms for handling such exposures exists.

4. Blood Exchange

Hemoglobin from blood follows the following steps of reactions within the photolytic cell.

Hb(h.s. Fe$^{II}$)+O$_2$→Hb(l.s. Fe$^{II}$)O$_2$

HbO$_2$+2H$^+$(pH 6.8–7.6)→H$_2$Hb2$^+$+O$_2$

N-of two alpha-chains (pKa~8.0) and His β146 (pKa~6.5) residues are bases for H$^+$ reaction

CO$_2$+H$_2$O+-H$_2$CO$_3$+-H$^+$+HCO$_3^-$

Hb(R—NH$_2$)+CO$_2$+-R—NH—COO$^-$+H$^+$

When water reacts with a light activated catalyst, the hydrogen ion that is released rapidly reacts with an HCO$_3^-$ ion and forms H$_2$CO$_3$. The photolytic cell has excess HCO$_3^-$ ions to react with hydrogen ions.

The photolytic cell allows the blood to achieve the proper mass balance. The mass balance of blood traveling through the photolytic cell is as follows:

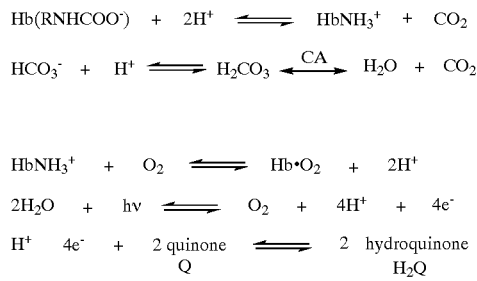

Net Reaction: Hb(RNHCOO$^-$)+HCO$_3^-$+H$^+$+H$_2$O+hv +2Q+-2CO$_2$+Hb.O$_2$+2H$_2$Q.

Alternatively, quinone can be replaced with Fe(CN)$_6^{3-}$. The quinone or Fe(CN)$_6^{3-}$Q could be in homogeneous solution or film form.

5. Cation Exchange Membrane 46

The cation exchange membrane 46 allows for the diffusion of cations in the photolytic cell. Particularly, the cation exchange membrane allows a cation, such as a sodium ion (Na$^+$) from blood to diffuse through the membrane and subsequently form sodium hydroxide (NaOH) in the catholyte. The cation exchange membrane is commercially available under the trademark NAFION® and is available from E.I. du Pont Nemoirs Inc. NAFION® cation exchange membranes are a perfluorosulfonic acid/PTFE copolymer in an acidic form. Although NAFION® cation exchange membranes are the preferred membrane, one skilled in the art would recognize that other cation exchange membranes are also suitable in the photolytic cell.

Anode

The anodic compartment of the photolytic cell has the following series of reactions:

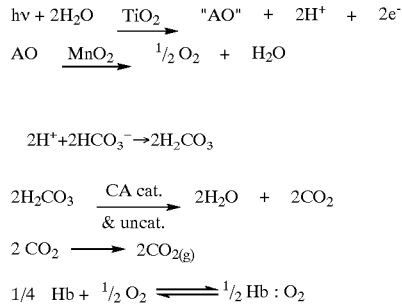

The overall net anodic reaction from the above reactions is as follows:

hv+¼Hb+2NaHCO$_3$→2CO$_{2(g)}$↑+H$_2$O+½Hb$_{0.5}$O$_2$+2e$^-$+2Na$^+$

The two electrons formed in the anodic reaction are conducted away to the cathode via the anode conductor layer. The two Na$^+$ ions are moved to a catholyte via a cation exchange membrane.

6. Catholyte 48

Sodium hydroxide (NaOH) builds in the catholyte during the series of reactions in the photolytic cell. It is preferred that the NaOH is purged occasionally from the catholyte. If sodium chloride (NaCl) is used in the catholyte instead of NaOH, NaCl(s) may eventually form within the catholyte and would periodically be purged.

The reactions occurring in the cathode of the photolytic cell are as follows:

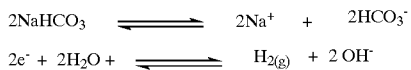
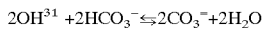

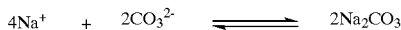
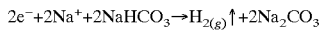

The overall net cathodic reaction is as follows:

$$2e^- + 2Na^+ + 2NaHCO_3 \rightarrow H_{2(g)}\uparrow + 2Na_2CO_3$$

The $Na_2CO_3$ that is produced causes pH to rise. Based upon the overall anodic and cathodic cell reactions, the overall net photolytic cell reaction is:

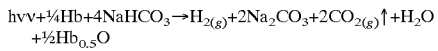

7. Battery/Current Regulator

As shown in FIG. 4, the photolytic cell can include a battery 49, current regulator 50, or resistor 52. An electrical current formed from a battery 49 allows electrons to flow from the anode 36 to the cathod 38. The intial bias voltage caused by the current supplied from the battery initiates the removal of electrons formed during the conversion of water to dissolved oxygen and prevents the electrons from reacting with the active or dissolved oxygen to reform water. The initial bias voltage also allows more dissolved oxygen to be produced as the removal of the electrons minimizes the reformation of water. Additional external electrical contacts can monitor or apply a particular voltage to the photolytic cell.

The current regulator and resistor help control the flow of electrons from the anode to cathode, thereby controlling the amount of dissolved oxygen formation. The resistor creates a fixed control in the current flow, whereas the current regulator can be adjusted to increase or decrease the resistance of the current flow. Increasing the resistance of the current lowers the number of electrons flowing from the anode to the cathode, thereby lowering the overall production of dissolved oxygen. Decreasing the resistance of the current increases the flow of electrons from the anode to the cathode, thereby increasing the amount of dissolved oxygen produced.

8. Optimal Gas Sorption Device 24

Continual venting of carbon dioxide gas out of the photolytic cell presents the problem of potential infection. A gas sorption device minimizes and provides control over potential infection risks by avoiding continuous venting of the $CO_2$ to the atmosphere. The gas sorption device captures $CO_2$ gas released from the oxygenated blood in a concentrated form. The concentrate can be processed or disposed of occasionally so that the sterility of the photolytic cell is not continuously subjected to possible contaminants due to the continual venting of the $CO_2$ gas.

$CO_2$ can be captured using a number of different ways by a gas sorption device 24. The gas sorption device can use the process of chemi-absorption and convert $CO_2$ into a concentrated solid or solution form. The concentrate formed in the gas sorption device can then be disposed of as disposable cartridges having liquid or solid $CO_2$, or regenerated.

Figure 5:
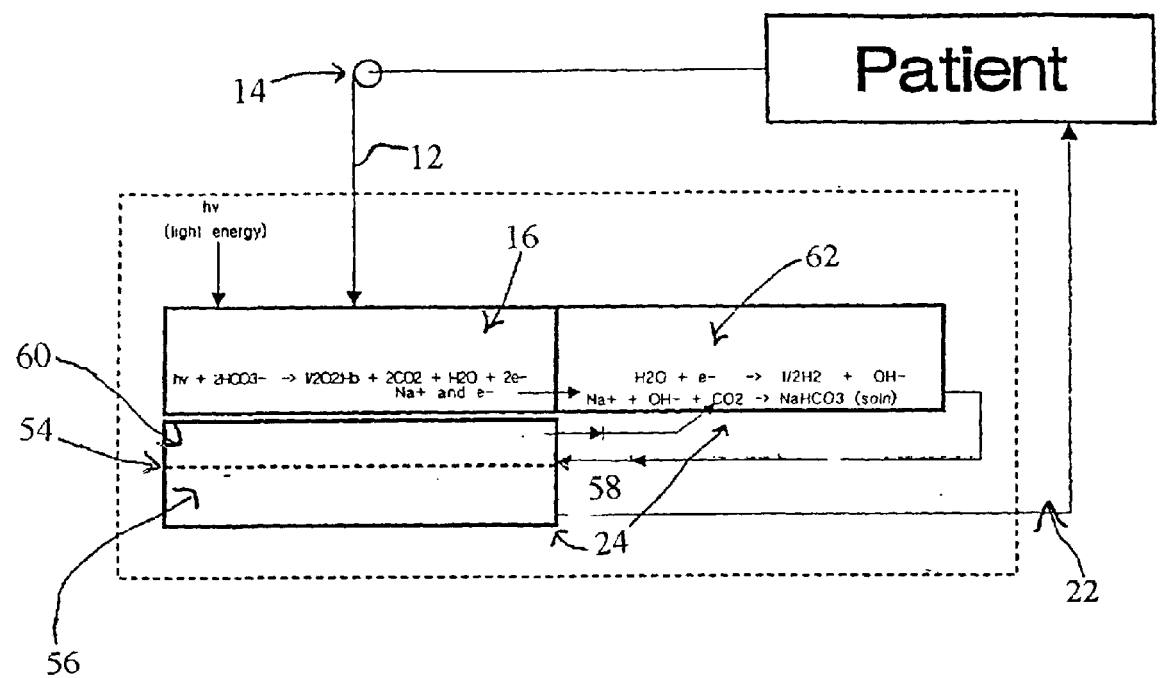
FIG. 5 shows a diagram of the gas sorption device.

FIG. 5 shows the general schematic of the gas sorption device 24 and path of $CO_2$ to the gas sorption device 24 for absorbing $CO_2$. The photolytic cell 16 forms dissolved oxygen that associates with the deoxygenated blood flowing through the cell. The $CO_2$ produced in the anode of the photolytic cell 16 from the conversion of bicarbonate ion to carbonic acid is present as small bubbles as a result of carbonic anhydrase activity. These bubbles are readily released within a coalescence compartment 54 so that the use of membranes are avoided. Four moles of $CO_2$ gas is released per mole of $O_2$ gas formed. When $O_2$ is formed at the targeted flow of 150 cc/min gas at STP, the moist $CO_2$ flow rate is about 600 mL/min at STP. $CO_2$ is trapped when entering the coalescence compartment 54 by a gas coelesor 56. In or near the bottom of the gas coalesor 56 an entry point 58 exists for hydrogen gas ($H_2$) coming from the cathodic compartment. The $H_2$ gas merely sweeps across the head space 60 above the gas coelesor 56 in the coalescence compartment 54 and collects $CO_2$ gas. The flow is provided by the same pump 14 that is used to provide the photolytic cell 16 with blood since the photolytic cell 16 is either a fully liquid-filled closed system, or a cascading overflow (but non-portable) system. The $CO_2/H_2$ gas mixture exits the top of the gas head space 60, near the blood entry point. When $O_2$ is formed at the targeted flow of 150 cc/min gas at STP, the $H_2$ flow rate is at least about twice the $O_2$ flow rate or 300 mL/min (STP). The gas mixture then flows to a sorber 62.

Figure 6:
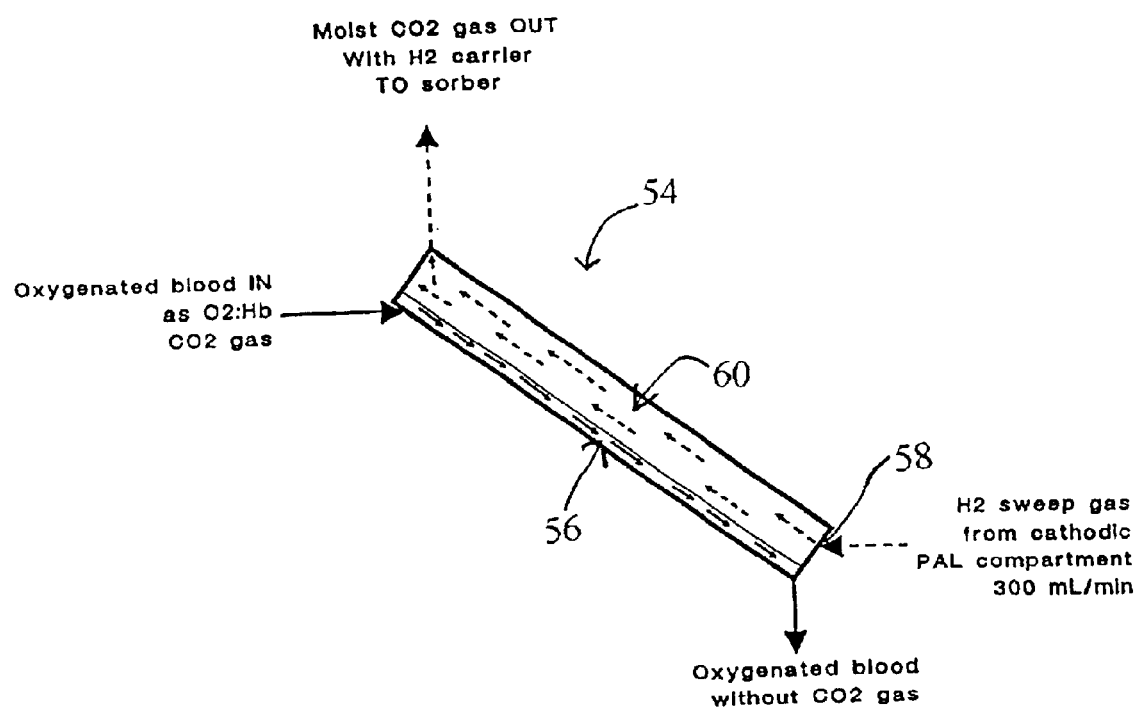
FIG. 6 shows a schematic diagram of the coalescence collector.

FIG. 6 shows a coalescence compartment 54. The coalescence compartment 54 can be a small plastic reservoir having a relatively small volume, and can be any shape. Preferably, the coalescence container 54 has a downward tilt. The whole blood travels through the coalescence container 54 through the coelesor 56 and returns to the patient at the bottom of the tilt. $H_2$ gas enters at an entry point 58 into the gas head space 60 and sweeps the $CO_2$ through the gas head space 60 and into a sorber (not shown). The coalescence container 54 can be used as a temperature control point.

Figure 7:
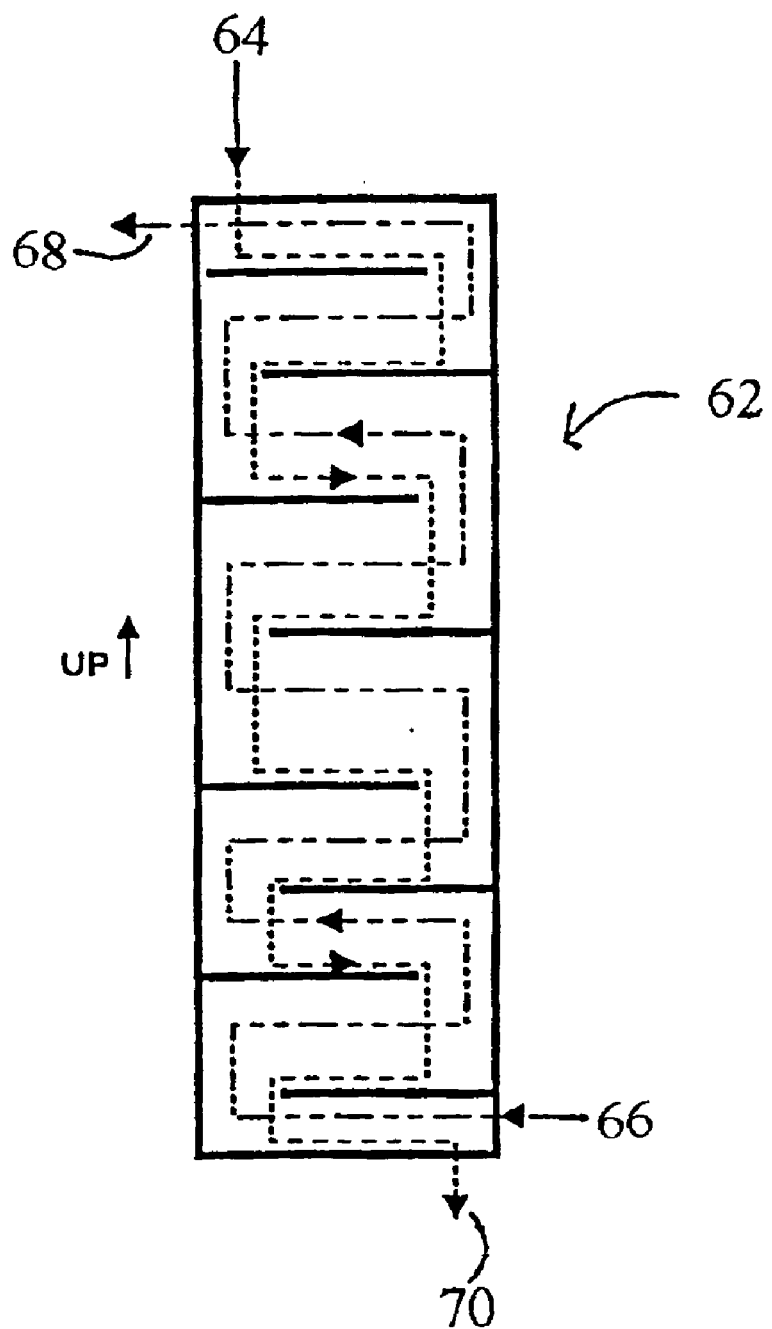
FIG. 7 shows an interior view of the gas sorber device.

FIG. 7 shows a sorber 62. The sorber 62 converts $CO_2$ gas into either a solution or solid depending on the sorbent 64 used within the sorber 62 without the need for mechanical mixing or pumping. The high capacity, low pressure drop, sorber 62 for $CO_2$ gas operates at mild pressure with a gravity feed and without the need for high surface area contactor. The $CO_2/H_2$ gas mix enters the sorber 62 at an entry point 66 near the bottom of the sorber 62. Intimate mixing of gas and liquid is accomplished by the 90° flow path changes, cross-path gas/liquid paths, and counter-current configuration. The $CO_2$ reacts with the sorbent 64 in the sorber 62 to form a solid or solution. The solid or solution formed can be removed through an outlet 70. Hydrogen gas can be swept out through a sweeping outlet 68 and be reused in the coalescence compartment (not shown). Preferably, the sorber 62 is small and has a total internal volume of about 25 cc. The entire sorber 62 is contained within the sterile unit. Since blood is not involved in the sorber 62, potentially detrimental effects in the blood are avoided. Also, the large orifices and membrane-free operation prevents potential fouling. The sorber 62 can have a vertical orientation but can also be designed with broad orientation accommodation. The entire sorber 62 is contained within the sterile unit.

The sorbent material 64 within the sorber 62 can be a solid or a solution. As a solution, the sorber can also be the catholyte for the photolytic cell. The sorbent 64 as a solution is consumed at a rate of 2–6 mL/min for the a $CO_2$ gas flow rate of 600 mL/min at STP. The high capacity, low pressure drop, sorber 62 for $CO_2$ gas operates at mild pressure with a gravity feed and without the need for high surface area contacter. Alternatively, the sorber 62 can use a solid sorbent 64 where the sorbent 64 is a packed bed of sorbent granules. Since blood is not involved in the sorber 62, potentially detrimental effects in the blood are avoided. Also, the large orifices and membrane-free operation prevents potential fouling. The sorber 62 can have a vertical orientation but can also be designed with a broad orientation accommodation. Sorbent materials are selected to react with the $CO_2$ gas to form bicarbonates and carbonates as solutions, solids, or combinations of these. Individual sorbents can be blended to obtain synergistic blends which, for example, might react faster, be more cost effective, and/or hold more carbon dioxide equivalents than the pure materials. Table 1 is a list of sorbent materials along with their $CO_2$ capacity equivalents.

regenerated continuously through the self sterilizing and self-cleaning caustic heating operation at mild temperatures and pressures. Alternatively, the sorbent can be continuously regenerated. For the carbonate sorbent system, the pH will vary from an initial pH of 11.6 to a pH of 8.3 when exhausted and could be monitored using a pH indicator dye or pH electrode.

Hydrogen gas produced in the cathode and used to sweep the $CO_2$ from the blood to the coalescence compartment will accumulate unless vented. $H_2$, being an extremely small molecule, readily diffuses through most non-metallic materials, especially plastics, ceramics, etc. The venting of $H_2$ can be controlled by selecting materials of construction that allow diffusion. No particular membranes, vessels, pumps, filters, one way valves, etc. are required to diffuse $H_2$. The role of $H_2$ as a sweep gas has a very broad range of acceptable flow rates for proper function since the $CO_2$ will self-flow in its absence and a negative pressure will develop in the $CO_2$ sorber as the chemistry is quantitative (CO2 efficiently absorbed down to low $P_{CO2}$ values).

8. Light Supply 20

The light supply is used in the photolytic cell to provide the photon energy necessary to activate the catalyst convert-

TABLE 1

Sorbent Solutions and Solids for $CO_2$

| Sorbent | Solution or Solid | solution density g/cc | % sorbent in solution (20–25° C.) | Maximum molarity of $CO_2$ when fully loaded or of sorbent initially charged. | $CO_2$ sorbing capacity | Chemical Form of Sorbed $CO_2$ |
|---|---|---|---|---|---|---|
| $Na_2CO_3$ | soln | 2.53 | 31.3 (35° C.) | | | $NaHCO_3$ |
| NaOH catholyte (w/OH— from PAL cell) | soln | 1.52 | 50 | 19.01 | | $NaHCO_3$ and $Na_2CO_3$ |
| NaCl catholyte (w/OH— from PAL cell) | soln | TBD | TBD | TBD | TBD | $NaHCO_3$ and $Na_2CO_3$ |
| KCl catholyte (W/OH— from PAL cell) | soln | TBD | TBD | TBD | TBD | $KHCO_3$ and $K_2CO_3$ |
| KOH catholyte (w/OH— from PAL cell) | soln | TBD | TBD | TBD | TBD | $KHCO_3$ and $K_2CO_3$ |
| $CaCl_2$ catholyte (w/OH— from PAL cell) | soln | | 40. | 5.03 | 5.33 cc/mi 320 cc/hr 7.7 L/hr | $CaCO_3(s)$ pKsp = 8.32 |
| $Ca(OH)_2$ | solid | TBD | TBD | TBD | TBD | $CaCO_3(s)$ pKsp = 8.32 |
| $MgCl_2$ catholyte (w/OH— from PAL cell) | soln | 1.28 | 30.00 | 4.021 | | |
| $Mg(OH)_2$ | solid | TBD | TBD | TBD | TBD | $MgCO_3(s)$ pKsp = 9.2 |
| soda lime | solid | TBD | TBD | TBD | TBD | $CaCO_3(s)$ pKsp = 8.32 |
| nonvolatile amines (e.g. MEA, DEA, etc.) | soln | TBD | TBD | TBD | TBD | $R_4N^+HCO_3$ |

(1) MEA and DEA are monoethanol amine and diethanol amine respectively. Polyol amines, polyamines, and zwitterionic materials are other suitable organic $CO_2$ sorbents.
(2) $CaCO_3$ is not expected to be regeneratable.
(3) Note that the halide salt systems, e.g. NaCl, KCl, $CaCl_2$ and $MgCl_2$, or mixtures thereof as are represented by brines such as Lockes-Ringer solution, saline solution, etc., sorb $CO_2$ by using the cathodically produced $OH^-$, the salt just providing charge balance at the membrane and electrode, and in the sorber/desorber.

$HCO_3^-$ loses $CO_2$ easily and the sorbent can be regenerated thermally, disposed of as a disposable cartridge, or ing water into oxygen. The light source can be from any known light source including, but not limited to, sunlight, UV light, laser light, incandescent light, etc., depending on the activation requirement for the light activated catalyst used. Preferably, the blood flowing through the photolytic artificial lung is not exposed to the light in order to prevent irradiation of the blood.

The light source may provide a particular wavelength of light depending upon the catalyst used. When tungstate ($WO_3$) is used as a light activated catalyst, the light source exposes visible light in order to activate $WO_3$. When $TiO_2$ or ZnO is used as a light activated catalyst, the light source used has a wavelength in the UV range.

Preferably, the light source used in the photolytic artificial lung is a laser light. The wavelength of laser light can be manipulated in order to attain a higher efficiency in exciting the light activated catalyst and forming active oxygen. Also, laser light allows the photolytic artificial lung to dissipate less overall heat. The laser light can be directed in a small area to energize the light activated catalyst and avoid contact or irradiation with other components of the photolytic artificial lung. A particularly preferred laser light that can be used to activate $TiO_2$ is an argon laser at 364 nm (400 $mwatts/cm^2$), which has a total power of about 2 watts, although other UV sources, including an HG arc lamp at 365 nm line, are also available.

It is preferred that the light from the light source be evenly spread within the photolytic cell. The even spreading of the light from the light source allows for maximal excitation of the catalyst in order to convert more water into either active oxygen or dissolved oxygen. Along these lines, light from the light source can enter the photolytic cell through the transparent window from many positions. Light from the light source can enter directly through the transparent window and come into contact with the catalyst. Alternatively, light can enter the transparent window from a side, back, bottom, or corner position and move through the transparent window by a wave guide to provide photon energy and excite the light activated catalyst. Side entry of light into the transparent window of the photolytic cell occurs at about at least a 68° angle. Preferably, side entry of light into the transparent window occurs at an angle of from about 70° to about 80°.

9. Pump

A peristaltic pump or some other simple pump drives blood through the photolytic artificial lung. The pump draws venous deoxygenated blood from a patient and moves the blood through the photolytic artificial lung. Preferably, the photolytic artificial lung only requires a pump to draw blood from a patient, as the flow produced by the pump drawing blood from the patient also moves the blood through the photolytic cell for oxygenation and back into the patient.

10. Sensors Monitoring Reaction Chemistry

The photolytic artificial lung can include one or more sensors that monitor the different chemical reactions occurring within the photolytic cell. The sensors can be used to measure for potential toxins and toxin levels. Various sensors and sensor systems can be used including visual observations of color changes of redox indicator dyes or gas bubble formation, closed electrical current measurements and pH measurements, and dissolved oxygen probe analysis. Gas chromatography assays can also be performed. A dissolved oxygen probe can be used to test and monitor $O_2$ generation, as dissolved oxygen, in real time. Also, the photolytic artificial lung can incorporate one or more portals to insert a dissolved oxygen probe, $CO_2$ probe, pH monitor, etc. in different locations if necessary. The photolytic artificial lung can also incorporate separate sampling chambers to trap gas bubbles for testing. These sampling chambers could also incorporate a device, such as a septum for a hypodermic needle for instance, to obtain a sample for further testing. One skilled in the art would recognize numerous sensors could be used for monitoring the reaction chemistries occurring within the photolytic cell.

The photolytic artificial lung and photolytic cell can also include one or more process regulator devices that respond to the readings provided by the sensors. The process regulator devices increase or decrease the amount of dissolved oxygen or $CO_2$ output, lower toxin levels, etc., depending on the requirements of the patient or of the photolytic cell. It is within the purview of one utilizing the photolytic artificial lung to determine what process regulator devices are required.

All of the seals in the photolytic artificial lung are made of an inert material that properly seals blood flowing through the photolytic artificial lung from accidental contamination. The seals of the photolytic lung should also be formed of a material that does not interact with the blood. Preferably, the seals are formed of a silicone-based material.

Laminar flow is minimized within the photolytic artificial lung. Minimization of laminar flow is accomplished by using current commercial cells, such as electrodialysis, electrodeionization, etc. Commercially available cells accommodate electrodes, membranes, and thin liquid chambers with flow distributors, and provide good seals and corrosion resistance. The cells are available in lab scale units for process development work. A particularly preferred commercial cell is the FM01-LC device from ICI Chemicals and Polymers, Electrochemical Technology, Cheshire, UK.

Multiple Photolytic Cells

Preferably, the photolytic artificial lung uses a plurality of photolytic cells in a stacked formation. The plurality of photolytic cells receive blood flow from the venous circulation and are exposed to photo-activation via a directed laser light source. The stacking of a plurality of photolytic cells allows for a large overall surface area for blood to receive maximal exposure to dissolved oxygen. Also, stacking a plurality of photolytic cells allows the overall photolytic artificial lung to achieve a smaller size, thereby allowing the photolytic artificial lung to be miniturized.

Photolytic Cell has Broader Applications

The photolytic cell as described may be used for photochemical processes beyond the preferred embodiments described above. The photolytic cell may be used in other organs to cause or regulate chemical reactions occurring within the system. The photolytic cell may be used in organs including, but not limited to, heart, lungs, brain, kidney, liver, etc. Alternatively, the photolytic cell may be used outside of a biological system in order to control reactive activity. Also, one having ordinary skill in the art would recognize that the photolytic cell could also be used as a potential energy source due to the production of electrons.

EXAMPLES

Having generally described the invention, the following examples are included for purposes of illustration so that the invention may be more readily understood and are in no way intended to limit the scope of the invention unless otherwise specifically indicated.

A prototype photolytic artificial lung was produced in order to demonstrate the ability of the device and accompanying processes to re-oxygenate synthetic blood serum (Locke's Ringer Solution), with concomitant $CO_2$ removal and pH control, using thin film constructs. In this regard, a photolytic test flow cell (see FIG. 3) was constructed using exemplar materials for the elements of the photolytic artificial lung—a conductive coating of vacuum deposited Ti metal, a coating of adherent $TiO_2$ (anatase), a $MnO_2$ particulate layer, and then a bicarbonate solution. A U.V. laser light was introduced to the transparent glass or quartz substrate. This cell was used to collect pH and cell electrical current data as a function of laser U.V. irradiation. The details of the construction of such a prototype and the results produced thereby are discussed below.

In this regard, a photolytic test flow cell as shown in FIG. 3 of the photolytic artificial lung was prepared. Specifically, among other components the following layers of the photolytic cell were assembled: light source 20; transparent window 30; e⁻ conductor (anode) 36; $TiO_2$ photo catalyst 32; $MnO_2$ catalyst 34; NAFION® cation exchange membrane 46; catholyte 48; and conductor (cathode) 38. The particular parameters of these components and others are as follows:

Glass/Quartz Slide 30 Preparation

A glass slide was degreased by swirling in toluene or MEK. The slide was flash dried in air for less than about 1 minute. The slide was then soaked in warm Micro® cleaning solution for about 2 minutes. The slide was rinsed thoroughly with 18 MΩ DI water. The slide was immediately thereafter soaked in a water bath for about 2 minutes. The slide was rinsed thoroughly with water from a squirt bottle and drained but not allowed to dry. With caution, the slide was submerged in a solution of concentrated sulfuric acid and was allowed to stand for 2 minutes. A plastic hemostat was used to hold the slide when it is inserted/withdrawn from the sulfuric acid. The slide was withdrawn, allowed to drain, and rinsed thoroughly with water. The slide was then soaked in a water bath for about 2 minutes. A water break test was then performed on the slide. Using a plastic (Nalgene®) beaker with cover watch glass, the slide was dipped for 2 minutes in a solution of 0.1% HF and 1N HCl. The surface of the glass now contained Si—OH linking groups. These slides were kept wet, and stored in 5% $HNO_3$.

Catalyst Layer 32 Preparation

About 1.0 g of $TiO_2$ (anatase) was added to a plastic (Nalgene®) beaker with a cover watch glass, and a magnetic stir bar. In a hood, 80 mL of 0.1% HF and 1N HCl was added to the $TiO_2$. A stirrer stirred the beaker until the solids were well suspended. The beaker was mixed for 60 seconds and was proceeded immediately to the next step of dividing the slurry between two 50 mL capped centrifuge tubes. The tubes were centrifuged for at least 5–10 minutes. The supernatant was discarded. Each tube was rinsed 3 times with 40 mL portions of water. The tube was capped, vortexed thoroughly, centrifuged, decanted, and the steps were repeated. Each tube was rinsed 3 times with 40 mL portions of isopropanol (iPrOH). Optionally, one or more inorganic silane and/or titanate-coupling agents can be added to the last alcohol rinse to facilitate agglomeration and adhesion in the final coating. The aggressive oxidizing environment of the UV/$TiO_2$ during use may rapidly degrade organic-based coupling agents and so inorganic couplings may be favored.

Application of the Catalyst to the Glass Slide

The pretreated $TiO_2$ anatase particles were magnetically re-suspended from one of the tubes in a jar containing isopropanol sufficiently deep to cover the glass microscope slide. Magnetic stirring was initiated to keep the particles suspended. The amount of particles used is an adjustable parameter in determining the thickness of the final coating produced.

A sufficient amount of $Ti(iOPr)_4$ (TTIP) was added to yield a 0.2 vol % solution (e.g., by adding 160 uL TTIP per 80.0 mL isopropanol). Using a plastic hemostat to hold the slide, the treated glass slide was rinsed thoroughly with water and was again tested under the water break test. The slide surface was rinsed thoroughly with isopropanol. The slide was soaked for 2 minutes in isopropanol and rinsed again with isopropanol. The slide was immediately hung in the TTIP/isopropanol solution and stirred. The vessel was covered to minimize pickup of moisture from the air, and allowed to react for about 120 seconds. During this time, the TTIP reacted with the Si—OH groups on the surface of the glass slide to form O—Si—O—Ti-iOPr linkages, although the linkages may not have formed rapidly until the heating step below. The slide was removed very slowly (e.g. 1 cm/min) using the hemostat and was laid flat on an inverted bottle cap in a vacuum desiccator to dry for a few minutes. The standing time in the room air (humidity level and contact time) was adjustable since water vapor diffuses to the surface of the slide causing hydrolysis reactions (the "sol" in sol-gel), i.e.,

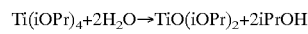

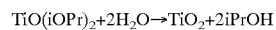

Excess water must be avoided so that the silanol groups on the surface of the slide may react, i.e.,

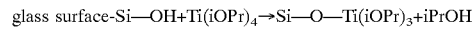

Similar reactions couple the $TiO_2$ anatase particles to the surface of the glass and to each other,

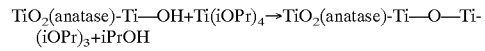

It is noted, however, that thoroughly desiccated (water-free) surfaces are also not useful since dehydration of surface Si—OH and Ti—OH groups occurs, which would remove the hydrogen needed to produce the iPrOH product at low energy. The time spent at this room temperature condition can be adjusted since the coating slowly reacts during this time.

While still lying flat, the slide is oven-dried at 80–90° C. for 20 minutes to finish the cure. The time, temperature and heating rate (° C./min) parameters are adjustable. Heating too fast can blow out solvent, causing massive disruption of the film due to out gassing, while heating too high a temperature can cause too much condensation resulting in shrinkage, leading to pulling away of the film and cracking. Porosity is expected to be important so that water can penetrate and active oxygen can leave the reaction zone.

In order to obtain slides having a thicker $TiO_2$ coating, the above steps are repeated one or more times.

The slide was heated to 250° C. for two hours to fully cure and set the coatings. This temperature was needed to convert the amorphous $TiO_2$ formed from the TTIP into anatase. *Ind. Eng. Chem. Res.* 1999 38(9), 3381. Alternatively, a slide can be pretreated as above except heat the coating to 350° C. at the rate of 3° C./min and hold at this temperature for 2 hr. Miller, et al. *Environ. Sci. Technol.* 1999, 33, 2070. Another alternative is to prepare the sol-gel solution in place of the anatase/TTIP slurry. Colloid C in Aguado, M. A., et al., *Solar Energy Materials. Sol. Cells,* 1993, 28, 345. The slide was then removed and allowed to cool to room temperature.

The coating adhesion of the $TiO_2$ anatase to the glass slide was tested by abrasion with a rubber policeman, tape test, etc. Also, the coating adhesion was tested for other properties including thickness, tendency to crumble/flake off, visual appearance, etc.

The experiments were repeated as needed to improve adhesion and other properties. An additional step of a 400° C. treatment for one hour can used to set $TiO_2$ (anatase) particles onto a quartz sand slide (Haarstrick, et.al. 1996).

$TiO_2$ Coating Photochemistry Testing

Two $TiO_2$ coating photochemistry testing procedures were conducted, the first to determine whether electrons were generated and the second to determine whether active oxygen was generated. First, the $TiO_2$ was tested by a negative charge/electron generation test. Methyl viologen ($MV^{2+}$) blue color ($MV^+$) was applied onto the anatase coating and was subjected to laser light. A rapid appearance of dark blue color qualitatively, validating electron formation. $MV^+$ blue color was not permanent since $MV^+$ is a free radical/charge transfer complex, which easily releases $e^-$ and returns to colorless ground state. Dried coating inhibited the performance of coating (dried minerals block surface sites), but was easily cleaned.

A second test conducted on the $TiO_2$ coating layer was the active oxygen generation test. Methylene blue was used on the $TiO_2$ coating to determine the presence of active oxygen. The methylene blue color was rapidly destroyed at the point of the laser light in the presence of anatase coating, validating active oxygen formation, since oxidized oxygen reacts with methylene blue.

Light Source

The light source used was an argon laser at 364 nm line (400 mwatts/cm$^2$) available (tunable to lower powers). The argon laser used has a total power of 2 watts. Alternatively, a number of UV sources were available for use, including Hg arc lamps using a 365 nm line.

Anode Conductor Layer 36

The anode conductor layer was formed by placing a very thin film of uniform metallic conductor having a thickness of less than about 0.2 μm using e-beam vapor deposition onto a transparent window. The thin film was formed of Ti metal. Conductor line spacing, width and thickness optimization may be required for the anode conductor layer to prevent excessive attenuation while provide sufficiently close conductive areas to sweep electrons away from $TiO_2$ layer.

Dissolved Oxygen Generating Catalyst Layer 34

A dissolved oxygen generating catalyst layer was formed from $MnO_2$ particles onto the surface of the $TiO_2$ (anatase) layer. The $MnO_2$ particles were applied (<5 u) as a iPrOH slurry with or without the anatase/Ti(iPrO)4 mixture. A significant surface of the $TiO_2$ (anatase) layer was coated (~⅓) by the $MnO_2$. Adding the $MnO_2$ drop wise and allowing it to evaporate was effective. The $MnO_2$ was added to increase % surface area covered by $MnO_2$ particles and to make the $MnO_2$ more adherent using the $Ti(iOPr)_4$ binder.

Flow Through Cell

The flow through cell was designed with fluid inlets and outlets on the same side. Silicone gaskets and spacers, acrylic external housing and stainless steal tubing connectors were used in forming the flow through cell. In the flow through cell, the anode was the continuous Ti plate and the cathode was a platinum foil strip.

Electrical Connection of Flow Through Cell

The electrical connection of the flow through cell was wired as an open circuit with a current meter and current regulator inline. The electrical connection of the flow through cell could also be formed by applying bias voltage added with the in-line current meter and current regulator. The electrical connection of the flow through cell could also be formed by placing a resistor and a current meter inline with a voltage reading across the resistor.

Divided Cell

A divided cell was designed with both sets of fluid inlets and outlets on the same side with the through-anode, through-acrylic housing and silicone spacer internal flow paths and on the side opposite the glass slide. The divided cell was further designed to include silicone gaskets or spacers, acrylic external housing, NAFION® membrane, and stainless steel tubing connectors.

Active Oxygen Testing

A Locke's Ringer saline test solution was prepared with 150 ppm redox dye (methyl viologen, $MV^{2+}$). Also, a 10 uM solution of methylene blue was prepared in the Locke's Ringer solution. Matthews, R. W., *J. Chem. Soc., Faraday Trans.* 1, 1989 85(6), 1291. The molar absorbtivity for methylene blue at 660 nm is 66,700±350 cm$^{-1}$M$^1$. The coated test slide was assembled with an attached UV lamp/laser. The Locke's Ringer solution was then added to the coated test slide via a circulating pump. After steady conditions were attained, the coating was illuminated directly/indirectly with UV light. The saline solution was monitored for appearance of blue color ($MV^{2+}$(colorless)+e-→$MV^+$ (blue)) and dissolved oxygen. Gas samples were sampled for GC assay ($CO_2$, $O_2$ not due to air).

Results

Figure 9:
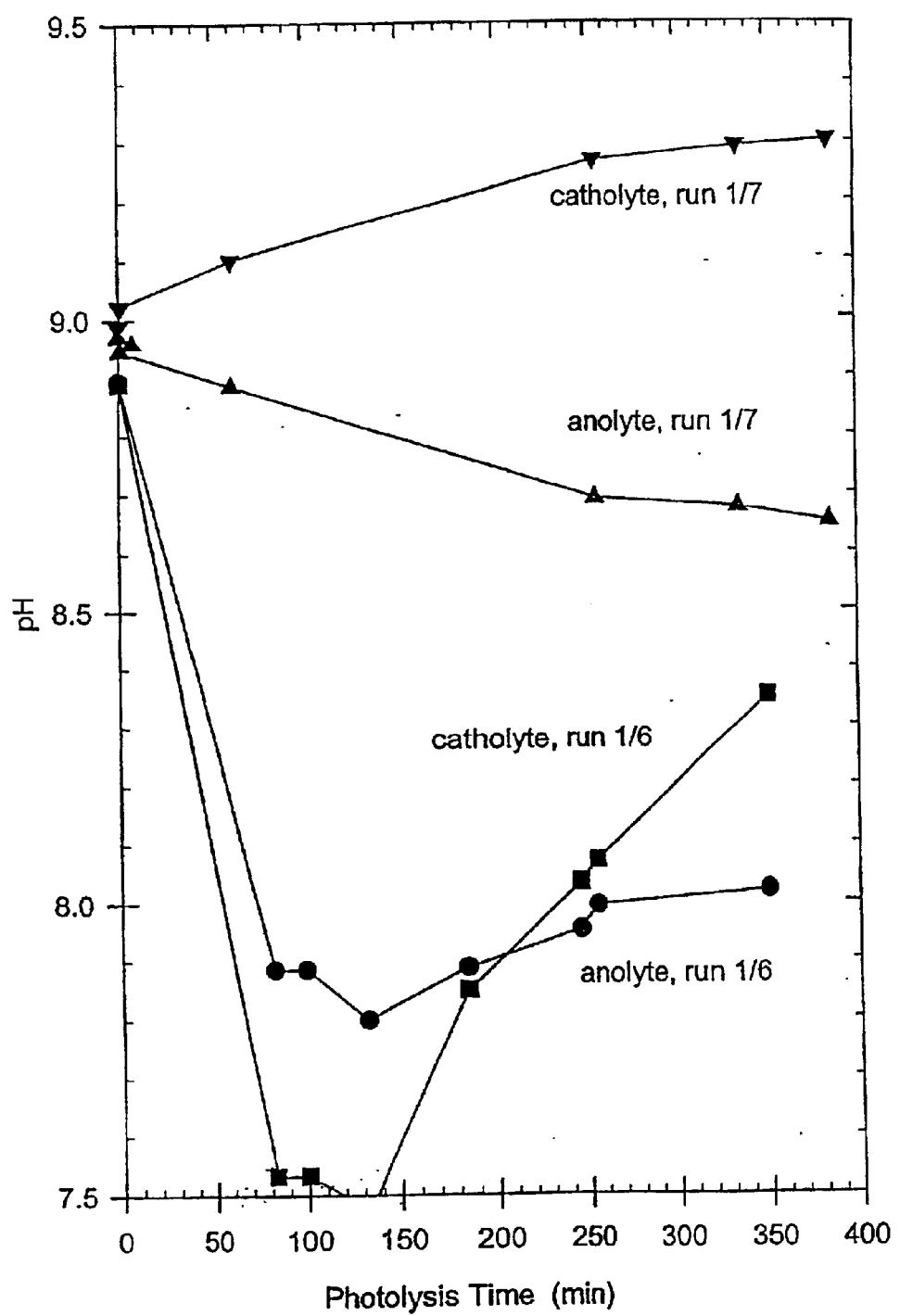
FIG. 9 shows a graph illustrating the relationship of the pH profile of the anolyte and catholyte during photolysis using the photolysis cell.

The artificial lung was tested in order to determine whether the chemical formulations occurred as predicted. The testing was conducted using Locke's Ringer solution, which is a saline solution that mimics blood. The qualitative results of the testing are as follows:

1. Highly efficient U.V. light absorption by thin films of $TiO_2$ (anatase) to impart energy into the anatase matrix was visually apparent in that the UV light is substantially absorbed. Attenuation by any metal conducting film present was measured and corrected separately.
2. Generation of active oxygen (AO) at the anatase surface using the energy from the UV light was evidenced by methylene blue dye disappearance at the surface of the anatase film opposite the side irradiated by the UV laser.
3. Generation of free electrons ($e^-$) at the anatase surface using the energy from the UV light was evidenced by methyl viologen blue dye color appearance at the surface of the anatase on the side opposite the side irradiated and only at the location of irradiation.
4. Transport of the free electrons ($e^-$) generated above to a conductive Ti anode surface, which were then swept away so that the free electrons do not recombine with the active oxygen also produced above was evidenced by electrical current in the anatase semiconductor film, to a metallic collector, wire and amp meter. The electrical current was found to flow only when the laser was on and the electrical current never flowed when the laser was off. The effect was observed through numerous off/on cycles, and the electrical current measured was proportional to the laser intensity up to a saturation point.
5. The release of hydrogen ions ($H^+$) and pH drop was found for the anodic compartment in a continuously circulated and irradiated cell. The opposite pH change was found for the cathodic compartment, which was consistent with the pH effect expected when water is separated into active oxygen and hydrogen ions at the anatase surface. FIG. 9 shows a plot of the pH profile of the anolyte and catholyte during photolysis using the photolytic cell. The opposite trends in the plot are as predicted based on the photosynthesis mimic chemistry, decrease in pH in the anolyte and a pH increase in the catholyte. The lower initial pH in the catholyte in Run 1/6 reflects a startup condition with a slightly lower pH. Run 1/7 used a pre-equilibrated photolytic cell to remove any inconsistent readings during start up conditions.

6. The conversion of $HCO_3^-$ ions from the synthetic serum electrolyte, i.e., Locke's Ringer solution, into $CO_2$, was in part observed by the formation of more $H_2O$. $H_2O$ is the expected product to be formed along with $CO_2$ during the bicarbonate ion conversion to carbonic acid and ultimate conversion to $H_2O$ and $CO_2$ using the $H^+$ ions released during the formation of active oxygen. $CO_2$ production was measured by gas chromatography (GC) analysis of off-gases, or calculated from pH changes. The $CO_2$ level found by GC analysis was significantly greater than atmospheric level, further indicating the formation of $CO_2$.

7. The generation of alkalinity at the cathode and related pH change indicated that the free electrons produced during the reaction of water into active oxygen were conducted away from the anode and consumed in a non-$O_2$ reducing manner, i.e., by reduction of water to hydroxide ion and $H_2$ gas.

8. Generation of $O_2$ as dissolved oxygen from an $MnO_2$ catalyst coating on the anatase from an active form of oxygen added to the test media was found.

All of the verified steps appeared to react at good rates. Using the electrical current generated, a rough size for the photolytic cell unit for a 100 ml/min $O_2$ flow rate was calculated and found reasonable. Also, a number of coating fabrications were tested that were designed to allow $MnO_2$ particles, as a coating or dopant, to react with long-lived, soluble forms of active oxygen. These $MnO_2$ coatings were found to generate abundant quantities of dissolved oxygen under the testing conditions.

Calculating Size of Photolytic Cell Required

Figure 8:
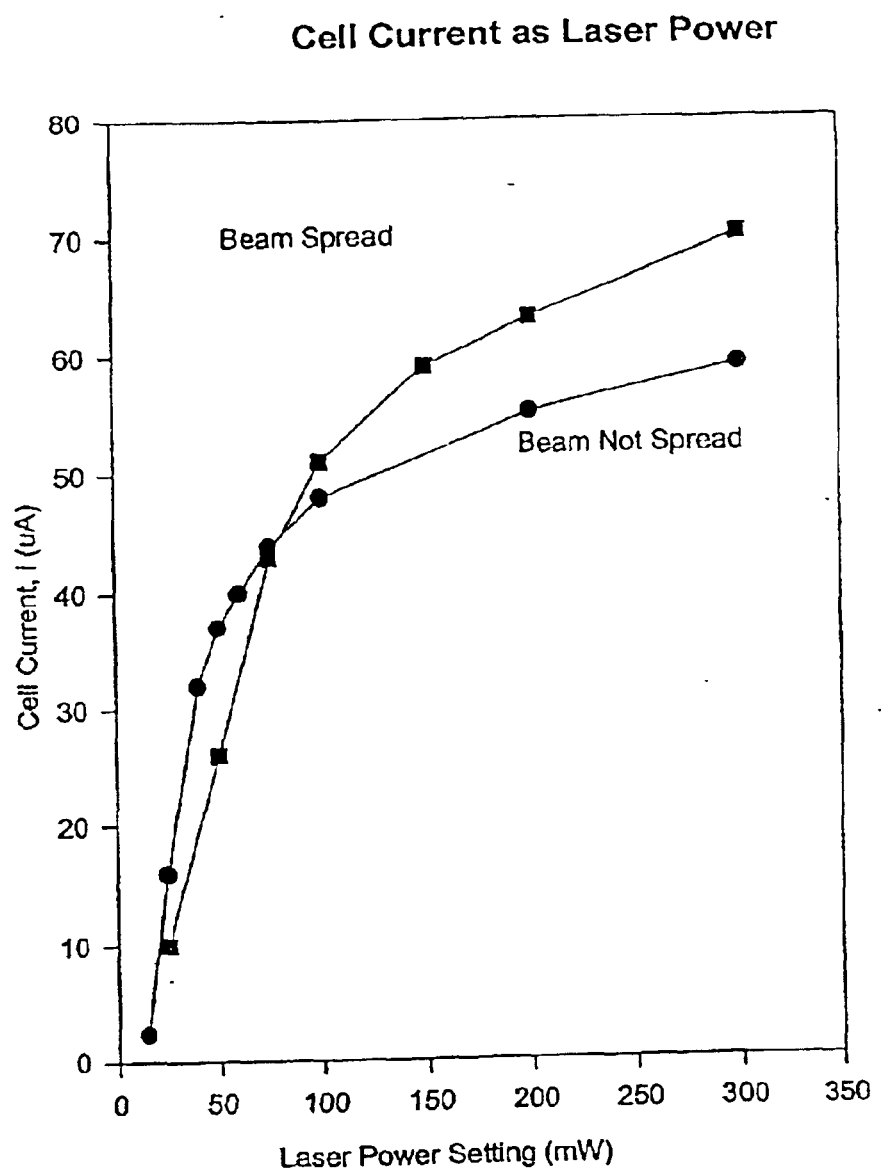
FIG. 8 shows a graph illustrating the plot of observed electrical current generated by the photolysis cell versus laser power intensity.

Preliminary testing was conducted on the photolytic cell to determine the size of a cell required to generate the target oxygen rate in an average adult human body of about 150 mL/min (STP) of $O_2$ for 5 L/min of blood flow, which is the average normal adult human blood flow rate. FIG. 8 shows the measure of the cell current versus the laser power setting in 0.60 g/L $NaHCO_3$ and 4% MeOH electrolyte. It is noted that the laser power setting is not the same as the actual impinging laser beam energy, but rather the laser power setting is greater than and proportional to the actual laser beam energy by a factor of about 2. Also, the power setting is of the laser itself and not of the 363.8 nm beam after it is separated from the other two lines produced by the laser. The laser power setting was measured after the laser moved around the optics bench and penetrated the glass slide and Ti collector film Although the data in FIG. 8 represents early exploratory testing and is far from optimized, it was used to calculate the size of a cell that would be needed to generate the target oxygen rate, 150 mL (STP)/min. From FIG. 8, a limiting cell current density of 70 uA/cm² can be estimated. Using this value, a cell surface area needed to generate 150 cc $O_2$ gas/min (STP) was calculated. If one flat sheet cell were used in contact with the blood, it would need to be 7.5×7.5 meters in area (56 m²) to provide 150 mL $O_2$ gas/min. Since no optimization has been done to date which might improve rates and since stacking of smaller plates to achieve a net large surface area is routine in electrochemical cell technology, this level of performance is considered encouraging as an early test result. Although the quantum efficiency was not determined in this qualitative testing, it appeared to be low. Many options are available to improve on the quantum yield. An improvement of 10 times would require a blood contact area (BCA) of 75 cm on a side, which then could be cut in half (by area) to 53 cm square by double siding the cell, i.e., one cathode, two anodes. Using six pairs, as is done in automotive batteries for example, reduces these dimensions to a cube of about 20 cm on a side, well within acceptable dimensions for an emergency use extracorpreal device without ancillary equipment. Therefore, a sufficiently small photolytic artificial having a small stack of photolytic cells appears possible with a 10 time improvement over the current production rates, assuming a high correlation between cell electrical current and is dissolved oxygen production. Reasonable target values for optimized photo current efficiencies are expected to be in the 0.1–10% range.

FIG. 8 also shows that spreading the laser beam to about 1 cm² resulted in about the same current production as did leaving the beam as a 3–4 mm spot. This result suggests that the photons were being supplied faster than they could be consumed. Therefore, significantly enhanced utilization of the laser power appears possible. Efficiency enhancements might be accomplished by pulsing the beam to allow the chemical reactions to keep up and/or further spreading it using optics.

The invention has been described with reference to the preferred embodiments. Obviously, modifications and alterations will occur to others upon a reading and understanding the preceding detailed description. Particularly, it is clear to one having ordinary skill in the art that the photolytic cell can be modified and used in numerous other reactions and reaction systems. It is also apparent that the present photolytic cell can be used in organs other than the lungs, and that the cell can be used in living systems other than humans. Furthermore, one skilled in the art would appreciate based upon the preceding detailed description that the photolytic cell can be used in forming chemical reactions in solutions other than whole blood. It is intended that the invention be construed as including all such modifications and alterations in so far as they come within the scope of the appended claims or the equivalents thereof.

Having thus described the preferred embodiment, the invention is now claimed to be:

1. A photolytic cell comprising:
   a transparent window;
   an anode conductor layer adjacent to said transparent window;
   a light-activated catalyst disposed upon said anode conductor layer;
   a cathode connected to said anode; and
   a catholyte bordering said cathode.

2. The photolytic cell of claim 1, wherein said light-activated catalyst is a metal oxide catalyst.

3. The photolytic cell of claim 1, wherein said metal oxide catalyst is $TiO_2$ anatase.

4. The photolytic cell of claim 1, wherein said cell further comprises a second catalyst disposed on said light-activated catalyst.

5. The photolytic cell of claim 4, wherein said second catalyst converts active oxygen to dissolved oxygen.

6. the photolytic cell of claim 1, wherein said photolytic cell converts water to oxygen.

7. The photolytic cell of claim 1, wherein said light-activated catalyst converts water into active oxygen.

8. The photolytic cell of claim 7, wherein said light-activated catalyst converts water into active oxygen.

9. The photolytic cell of claim 1, wherein electrons flow from said anode to said cathode.

10. A photolytic cell comprising:

a transparent window;

an anode conductor layer adjacent to said transparent window;

a light-activated catalyst disposed upon said anode conductor layer;

a cathode connected to said anode;

a catholyte bordering said cathode; and a second catalyst disposed on said light-activated catalyst;

wherein said second catalyst includes $MnO_2$.

11. A photolytic cell comprising:

a transparent window;

an anode conductor layer adjacent to said transparent window;

a light-activated catalyst disposed upon said anode conductor layer;

a cathode connected to said anode;

a catholyte bordering said cathode; and a cation exchange membrane abutting said catholyte.

12. A photolytic cell comprising:

a thin film of fiber transparent light conduit;

a substantially optically transparent electrical conducting film disposed adjacent to said transparent light conduit;

a light activated catalyst layer disposed upon said electrical conducting film;

an optically opaque anodic catalyst layer disposed upon said light activated catalyst layer, wherein said light activated catalyst is capable of producing hydrogen ions, electrons and oxygen;

an electrolyte flowing in contact with said anodic catalyst to accept the oxygen and hydrogen ions produced, and to supply by water molecules for their production;

an electrically conductive circuit to accept the electrons produced to conduct them to a cathode;

a membrane to transport cations from the electrolyte to a second electrolyte; and, a cathode to accept the electrons.

13. The photolytic cell of claim 12, wherein said photolytic cell converts water into oxygen.

* * * * *